US006884413B1

(12) United States Patent
Shearer et al.

(10) Patent No.: US 6,884,413 B1
(45) Date of Patent: Apr. 26, 2005

(54) INDUCTION OF ANTIGEN-SPECIFIC UNRESPONSIVENESS BY GLIOBLASTOMA CULTURE SUPERNATANTS (GCS)

(75) Inventors: Gene M. Shearer, Bethesda, MD (US); Jian-Ping Zuo, Shanghai (CN); John E. Coligan, Potomac, MD (US); Claire Chougnet, Batimore, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/936,537

(22) PCT Filed: Mar. 23, 2000

(86) PCT No.: PCT/US00/07959

§ 371 (c)(1),
(2), (4) Date: Sep. 12, 2001

(87) PCT Pub. No.: WO00/56356

PCT Pub. Date: Sep. 28, 2000

Related U.S. Application Data

(60) Provisional application No. 60/125,996, filed on Mar. 24, 1999.

(51) Int. Cl.[7] ......................... A01N 63/00; A61K 35/26; A61K 35/28
(52) U.S. Cl. ..................................... 424/93.1; 424/577
(58) Field of Search ................................. 424/577, 93.1

(56) References Cited

U.S. PATENT DOCUMENTS

| 4,728,614 A | 3/1988 | Lau |
| 5,095,095 A | 3/1992 | Fontana |
| 5,468,481 A | 11/1995 | Sharma et al. |
| 5,871,728 A | 2/1999 | Thomson et al. |

FOREIGN PATENT DOCUMENTS

| EP | 0 155 433 | 9/1985 |
| EP | 0 159 289 | 10/1985 |
| WO | WO 96/29394 | 9/1996 |

OTHER PUBLICATIONS

Dix A.R et al FASEB J, 1999, V13, N.4 pp. A 610.*
Zou et al J of Acquired Immune Deficiency Syndromes and Human Retrovirology, 1997, v. 14, p. A30.*
ATCC No.: CRL–1690; 2003.
ATCC No.: CRL–2020; 2003.
ATCC No.: CRL–2365; 2003
ATCC No.: CRL–2366; 2003.
ATCC No.: HTB–16; 2003.
ATCC No.: CRL–1620; 2003.
"TGF–beta 2 Antisense Gene Therapy for Glioblastoma," *Cytokine Bulletin*, Spring 1997.

Bluestone, "Transplantation Tolerance: The Next Frontier," *New Developments in Transplantation Medicine*, vol.1, Spring 1994.
Elliott et al., "Suppression of High Affinity IL–2 Receptors on Mitogen activated Lymphocytes by Glioma–Derived Suppressor Factor," *J. Neuro–Oncol.* 14:1–7 (1992).
Fontana et al., "Glioblastoma Cells Release Interleukin 1 and Factors Inhibiting Interleukin 2–Mediated Effects," *J. Immunol.* 132:1837–1844 (1984).
Mapstone et al., "Expression of Platelet–Derived Growth Factors, Transforming Growth Factors, and rosGene in a Variety of Primary Human Brain Tumors," *Neurosurg.* 28216–222 (1991).
Marquardt et al., "Complete Amino Acid Sequence of Human Transforming Growth Factor Type Beta 2," *J. Biol. Chem.* 262:12127–12131 (1987).
Morford et al., Apoptotic Elimination of Peripheral T Lymphocytes in Patients with Primary Intracranial Tumors, *J. Neurosurg.* 91:935–946 (1999).
Pisetsky, "11. Systemic Lupus Erythematosus. A. Epidemiology, Pathology, and Pathogenesis," in *Primer on Rheumatic Diseases*, pp. 100–105 (1977, v1.
Schwyzer et al., "Partial Purification and Biochemical Characterization of a T Cell Suppressor Factor Produced by Human Glioblastoma Cells," *J. Immunol.* 134:1003–1009 (1985).
Zou et al., "Human Glioma–Induced Immunosuppression Involves Soluble Factor(s) that Alters Monocyte Cytokine Profile and Surface Markers," *J. Immunol.* 162:4882–4892 (1999).

* cited by examiner

*Primary Examiner*—Christina Chan
*Assistant Examiner*—Michail Belyavskyi
(74) *Attorney, Agent, or Firm*—Klarquist Sparkman, LLP

(57) ABSTRACT

The present invention concerns methods of specifically inhibiting an immune response of a subject to one or more selected antigens using an immunosuppressive composition derived from a glioblastoma cell line. The method steps include obtaining a population of antigen presenting cells (APCs); loading the APC population with specific antigens (in auto-immune diseases) or using donor APCs (for transplantation); incubating the APC population with the immunosuppressive composition; and introducing the incubated cells into the subject being treated. The APCs can be monocytes, macrophages, or dendritic cells. This method causes specific inhibition of the immune response because it induces apoptosis and/or anergy in the subject's T cells specific for antigens present on the APCs, but does not affect the immune response to antigens not present on the APC surfaces. One particular embodiment of the present method is the specific inhibition of a transplant recipient's immune reaction to antigens present on the allogenic graft. A second particular embodiment of the present method is the specific inhibition of the immune response to an autoantigenic protein by a subject suffering from an autoimmune disease.

14 Claims, 13 Drawing Sheets

SAC stimulation for 24 hours

IDO-inhibitor (1-methyl-TRP) prevents GCS-pretreated monocyte-induced, PHA stimulated T cell apoptosis PHA stimulation (day 6)

INDUCTION OF ANTIGEN-SPECIFIC UNRESPONSIVENESS BY GLIOBLASTOMA CULTURE SUPERNATANTS (GCS)

PRIORITY CLAIM

This application is a U.S. national stage application of PCT/US00/07959, filed Mar. 23, 2000, which was published in English under PCT Article 21(2), which in turn claims the benefit of U.S. Provisional Application No. 60/125,996, filed Mar. 24, 1999.

FIELD OF THE INVENTION

This invention relates to an immunosuppressive composition and methods of using that composition to scaly inhibit the immune response of a subject to selected antigens.

BACKGROUND OF THE INVENTION

The normal mammalian immune system responds to the introduction of "non-self" antigens, such as antigens present on transplanted tissues, through a variety of complex mechanisms. One such mechanism is the recognition and destruction of such antigens by T lymphocytes (T cells), which selectively kill cells expressing "non-self" antigens, while leaving cells expressing only self antigens unharmed.

Antigen processing is necessary for any antigen to be recognized, and reacted to, by the immune system. For exogenous antigens, such as antigens present on transplanted tissue, processing begins with the uptake and fragmentation of the antigen by APCs. The antigen fragments associate with major histocompatability complex (MHC) proteins, specifically the class II type, and the combination "presents" on the APC surface. MHC class I proteins generally associate with antigens produced within the cell, such as viral proteins. The surface expression of two Co-simulators, CD 80 and CD 86, has also proven to be necessary for effective presentation of an antigen. T cells that express T cell receptors (TCRs) specific for the MHC/antigen complex and the receptor for CD 80/86, known as CD 28, are stimulated upon association with the APCs. The stimulation results in the production of cytokines and proliferation of T cells with that receptor specificity. The interaction between the specific T cells, the cytokines, and other components of the immune system selectively eliminate cells expressing the exogenous antigen, such as the transplanted tissue.

There are three general classes of APCs—macrophages, dendritic cells, and B cells. Dendritic cells are an important type of APC for stimulation with newly encountered antigens, and are likely to be important for rejection of transplant. Immature macrophages, or monocytes, are present in the circulating blood. Upon activation by stimulators such as interferons and bacteria (IL)-12, IL-10 and tumor neurosis factor TNF, among other immune regulators. Activation also results in the expression of MHC class I and II proteins and CD 80/86 on the cell surface. Dendritic cells are present in the skin and associated with lymphoid tissues throughout the body, and can be found in relatively low concentrations in the blood in different stages of maturation. The dendritic cells in the lymphoid tissue are found in association with T and B cell populations and are extremely effective presentors of antigens to these immune cells. Finally, B cells act as APCs through the binding of whole antigen molecules by surface antigen receptors, that are internalized and processed for presentation. Thus, processing and surface presentation by APCs can be thought of as a first step in the normal immune response.

Although immune recognition of "non-self" proteins is essential to avoid and eliminate infection, the immune response can sometimes be unwanted. Autoimmune diseases, such as rheumatoid arthritis, multiple sclerosis or insulin dependent diabetes mellitus, are the result of a pathological immune response against self antigens, and T cells are the primary mediators of autoimmunity. Rejection of transplanted organs and tissues are a further example of an undesired consequence of normal immunity, which can often result in damage to and/or rejection of the transplant.

Efforts have been made in the past to disarm the immune system using corticosteroids (such as methylprednisilone) or, cytotoxic drugs (such as cyclophosphamide), but the widespread and non-specific effects of these treatments often limit their utility or effectiveness. More specific immune modulators, such as FK506, have fewer undesired side effects, but still inhibit the entire immune response, rather than specific immune responses or responses directed to specific tissues. However, more recent efforts have been made to target particular molecular mechanisms of immunity to further refine the ability to modulate specific responses.

An impaired cellular immune response is a characteristic of many tumors in both animal models and human patients (Fujiwara et al., 1995 and Clerici et al., 1998). This diminished cellular immunity is not necessarily limited to reactivity against tumor-specific antigens, but can include unresponsiveness to non-tumor antigens and T cell mitogens (Mahaley et al., 1977 and Gruss et al., 1997). Cytokine dysfunction appears to contribute to tumor-associated immune dysregulation, with decreases of in vitro IL-2 and/or IFN-γ production and increases in IL-4, IL-5, IL-6 and/or IL-10 production.

Human gliomas provide an interesting example of tumor-associated immune dysfunction. The in vitro responses of T cells from patients who present with primary gliomas are impaired in their ability to respond in vitro to antigens and T cell nitrogens by proliferation and IL-2 production (Mahaley et al., 1977; Brooks et al., 1972; Elliott et al., 1984). Surgical removal of the primary tumor can result in restoration of systemic responses to T cell mitogens, which again decline with recurrence of the tumor (Brooks et al., 1981). Glioma patients also frequently fail to elicit delayed skin reactions (Brooks et al., 1972) and patients' T cells express reduced numbers of high affinity IL-2 receptors (Elliot et al., 1990a and Elliot et al., 1990b). It was recently reported that T cells from glioma patients exhibit defects in tyrosine phosphorylation of several proteins, reduced levels of PLCγ1 and p56$^{kk}$, as well as reduced mobilization of calcium (Morford et al., 1997). Other studies demonstrated that cultures of glioblastoma cell lines produce one or more factors that inhibit antigen- and mitogen-stimulated proliferation and IL-2 production by T cells from healthy individuals (Rozman et al., 1987 and Elliot et al., 1992).

SUMMARY OF THE INVENTION

One or more factors contained in glioma culture supernatant (GCS) exerts immunoregulatory effects on systemic cellular immunity, as well as at the site of the primary tumor. Although T cell proliferation and IL-2 production have been demonstrated to be defective in glioma patients and in cultures of PBMC exposed to GCS (Roszman et al., 1987), the possibility that these T cell defects have their origin in APCs, and the possible application of such a finding to the reduction of unwanted immune response to transplants or in the treatment of autoimmune disease, has not been addressed.

The present invention concerns methods of specifically inhibiting an immune response of a subject to one or more selected antigens using an immunosuppressive composition generated from a glioblastoma cell line. The method steps include obtaining a population of antigen presenting cells (APCs) such as purified or isolated APCs or APCs that have not been purified or isolated; incubating the antigen-pulsed APC population with the immunosuppressive composition; and introducing the incubated cells into the subject being treated. The APCs can be monocytes, macrophages, and dendritic cells. Optionally, the APCs may be exposed to an antigen against which selective immune inhibition is desired. Exposure to the antigen can result in the APC being "loaded" with the antigen. Without being bound by theory, this method causes specific inhibition of the immune response because it induces apoptosis and/or anergy in the subject's T cells specific for the antigens presented by the APCs, but does not affect the immune response to antigens not present on the APC surfaces.

Thus, a method of specifically inhibiting an immune response to one or more selected antigens is provided. The method includes providing antigen presenting cells (APCs) that present an antigen against which selective inhibition of an immune response is desired, and incubating the APCs with an immunosuppressive composition comprising one or more factors secreted by a glioblastoma cell line.

One particular embodiment of the present method is the specific inhibition of a transplant recipient's immune reaction to antigens present on the allogenic graft. In this case, the population of APCs is obtained from the transplant donor, and they express the transplant antigens responsible for rejection. Introduction of these APCs that have been incubated ex vivo with the immunosuppressive composition into the prospective recipient selectively depletes the patient of the T cells that would normally reject the transplant. A second embodiment of the present method is the specific inhibition of the immune response to one or more autoantigenic proteins or peptides in a subject suffering from an autoimmune disease. This embodiment involves obtaining APCs from the subject, and exposing the isolated APCs to peptide fragments of the autoantigenic protein of the autoimmune disease. These antigen-pulsed APCs are reintroduced into the subject in order to induce anergy and/or apoptosis in the T cells specific for the autoantigenic protein. Autoimmune diseases to be treated include, but are not limited to, multiple sclerosis (MS), rheumatoid arthritis (RA), myasthenia gravis (MG), systemic lupus erythematosus (SLE), and insulin dependent diabetes mellitus IDDM). The method would use the following autoantigenic proteins, among others: myelin basic protein (MBP), type II collagen, acetyl choline receptor (AcChoR), nuclear proteins, as defined below, and pancreatic islet cell surface antigens, as defined below.

In one embodiment, a method is provided for enhancing tolerance in a host mammal to an allogenic donor graft. The method includes providing mammalian APCs from a donor mammal and exposing the APCs to a therapeutically effective amount of a composition secreted by a glioblastoma cell, wherein the composition is effective to induce the APCs to secrete one or more factors that selectively inhibit clonal proliferation of a T cell that specifically recognizes an allogenic antigen presented by the APCs. A therapeutically effective dose of the APCs is administered to the host mammal to inhibit recognition of the allogenic antigen by the host mammal, by inhibiting the clonal proliferation of the T cell of the host mammal in response to presentation of the allogenic antigen by the APCs.

In another embodiment, a method is provided for making an immunosuppressive composition for suppressing an immune response to an antigen, including incubating a supernatant harvested from a glioblastoma cell culture and an antigen with an APC, thereby producing an immunosuppressive composition that includes the APC.

A substantially purified immunosuppressive composition is provided that includes one or more factors secreted by a glioblastoma cell line. Incubation of the composition with APCs presenting an antigen, and subsequent exposure of the incubated APCs to T-cells specific for the antigen, induces the T cells to undergo anergy and/or apoptosis. The factor or factors have molecular weights greater than about 40 kDa and show the ability to bind to anion, but not cation exchange columns.

In particular embodiments, the composition maintains the ability to induce T cells to undergo anergy and/or apoptosis within the pH range of 2 to 11, and following immunoprecipitation of TGF-β1, TGF-β2, TGF-β3, IL-6, and calcitonin gene related peptide (CGRP) from the composition. The composition loses the anergy/apoptosis-inducing ability following heat exposure above 56° C. or after exposure to trypsin. Furthermore, upon incubation of the composition with monocytes, dendritic cells, or B-cells there is decreased expression of MHC class II antigens and CD 80/86 on the surface of the monocytes and the dendritic cells, but no effect on the expression of MHC class II antigens and CD 80/86 on the B-cells. Incubation with the composition also increases expression of IL-10 and decreases the expression of IL-12 in monocytes and dendritic cells.

A method of making an immunosuppressive composition is provided. The method includes preparing a supernatant from a glioblastoma cell line, wherein the supernatant includes one or more factors secreted by the glioblastoma cell line. In particular embodiments, the composition has the following characteristics: a) incubation of the composition with APCs presenting an antigen, and subsequent exposure of the incubated APCs to T cells specific for the antigen, induces the T cells to undergo anergy or apoptosis; b) a molecular weight greater than about 40 kDa; c) ability to bind to anion, but not cation exchange columns; d) maintains an ability to induce T cells to undergo anergy or apoptosis under the conditions of a) within the pH range of 2 to 11, following heat exposure up to about 56° C., and following immunoprecipitation of TGF-β1, TGF-β2, TGF-β3, IL-6, calcitonin gene related peptide (CGRP), and M-CSF from the composition; and e) loses the ability to induce T cells to undergo anergy or apoptosis under the conditions of a) following heat exposure above 56° C., or after exposure to trypsin.

These features of the invention, as well as others, will become more apparent from the following detailed description of several embodiments and the accompanying figures.

DETAILED DESCRIPTION OF SEVERAL EMBODIMENTS

Abbreviations and Definitions

Figure 1:
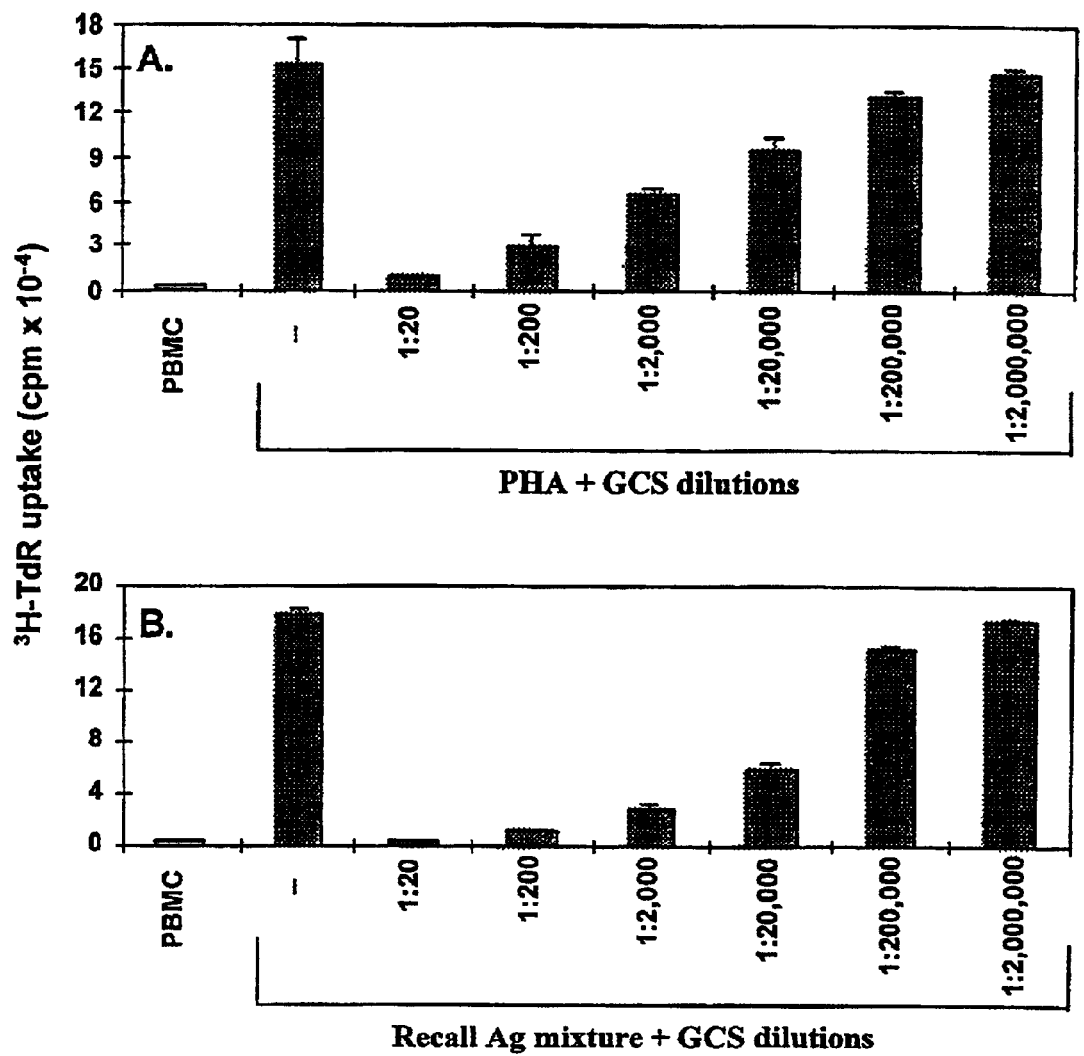
FIG. 1A is a graph showing GCS inhibits phytohemagglutinin (PHA) induced proliferation of peripheral blood mononuclear cells (PBMC) in a dose-dependent manner. The PHA-stimulated cultures were pulsed with $^3$H-thymidine after 2 days.
FIG. 1B is a graph showing glioblasoma culture supernant (GCS) inhibits proliferation of PBMC when induced by a pool of recall antigens consisting of influenza A virus (FLU), tetanus toxoid (TT) and candida (CASTA). The recall antigen-stimulated cultures were pulsed with $^3$H-thymidine after 6 days of culture. Four experiments were performed with PBMC from four donors each (n=3, cpm mean per minute SD), and the results shown are from one representative experiment.

The following abbreviations and definitions are used herein:

AcChoR: Acetyl Choline Receptor
Antigen: Antigen
APC: Antigen Presenting Cell
IDDM: Insulin Dependent Diabetes Mellitus
IL: interleukin
GCS: Glioblastoma Culture Supernatant
GM CSF: Granulocyte-Macrophage Colony Stimulating Factor
MBP: Myelin Basic Protein
M-CSF: Macrophage Colony Stimulating Factor
MHC: Major Histocompatability Complex
MS: Multiple Sclerosis
PBMC: Peripheral Blood Mononuclear Cells
PHA: Phytohemagglutinin
RA: Rheumatoid Arthritis
rIL: recombinant Interleukin
SAC: *S. aureus* Cowan strain 1
SLE: Systemic Lupus Erythematosis The following definitions and methods are provided to better define the present invention and to guide those of ordinary skill in the art in the practice of the present invention. It must be noted that as used herein and in the appended claims, the singular forms "a", "an", and "the" include plural referents unless the context clearly dictates otherwise. Thus, for example, reference to "a cell" includes a plurality of such cells and reference to "the antibody" includes reference to one or more antibodies and equivalents thereof known to those skilled in the art, and so forth.

Unless defined otherwise, all technical and scientific terms used herein have the same meaning as commonly understood to one of ordinary skill in the art to which this invention belongs.

Allogeneic: A genetic difference between individuals of the same species. Allogeneic cells are cells from one individual of a species that is genetically different from cells of another individual of the same species. In one embodiment, the genetic differences are differences in the major histocompatability complex on lymphocytes from gentically non-identical individuals of the same species.

Anergy: The functional inactivation of lymphocytes on encounter with an antigen.

Antigen: Any substance or material that is specifically recognized by an antibody or a T cell receptor. In one embodiment, an antigen is an immunogen that induces a specific immune response (an immune response directed against that antigen).

Antigen Presentation: The formation of a noncovalent interaction between an antigen and major histocompatibility (MC) class I or class II molecules at the surface of a cell, which allows recognition of the antigen by MHC-restricted T cells and the generation of an antigen-specific immune response.

Antigen Presenting Cell: An "antigen presenting cell" or "APC" is one of any of a number of different cell types that can process protein antigens and express them as peptide fragments complexed with class II major histocompatibility complex (MHC) molecules at the cells surface and are thus capable of activating antigen-specific T cells and generating an immune response. In one embodiment, an APC is of the macrophage/monocyte lineage. In another embodiment, an APC is a dendritic cell. In yet another embodiment, an APC is a B cell or a thymocyte that can express class II MHC molecules. An "APC mediated immune response" is an immune response that involves the presentation of antigens on an APC.

Selective Immune Response: An immune response against a particular antigen, such as a peptide antigen. An immune response is specifically inhibited if a parameter of the immune response (e.g. B cell activation, T cell activation, or cytokine secretion) is decreased in the presence of the compound, as compared to the parameter of the immune response in the absence of the compound. Similarly, a compound or molecule is "immunosupressive" if it decreases a parameter of an immune response, as compared to the parameter of the immune response in the absence of the compound or molecule.

Isolated: An "isolated" biological component (such as a cell type, nucleic acid, peptide or protein) has been substantially separated, produced apart from, or purified away from other biological components of the organism in which the component naturally occurs, i.e., other cell types, chromosomal and extrachromosomal DNA and RNA, and proteins. Thus an isolated cell has been substantially separated from other cell types of the organism in which the cell naturally occurs.

Purified: The term purified does not require absolute purity; rather, it is intended as a relative term. Thus, for example, a substantially purified peptide preparation is one in which the peptide or protein is more enriched than the peptide or protein is in its natural environment within a cell. In one embodiment, a preparation is substantially purified such that the protein or peptide represents at least 50% of the total peptide or protein content of the preparation. In another embodiment, a preparation is purified such that the protein or peptide represents at least 70% of the total peptide or protein content of the preparation. In another embodiment, a preparation is purified such that the protein or peptide represents at least 90% of the total peptide or protein content of the preparation. In another embodiment, a preparation is purified such that the protein or peptide represents at least 95–99% of the total peptide or protein content of the preparation.

Subject: an organism such as a mammal undergoing treatment, including both human and veterinary subjects.

T Cell: A class of lymphocytes which mediates immune recognition and effects cell mediated immune responses. In general T cells recognize protein antigens after they have been processed into peptide fragments and become associated with major histocompatibility complex molecules on the surfaces of antigen-presenting or target cells. T the cells can be classified by their function and include helper T cells, suppressor T cells, and cytotoxic T cells.

T Cell Activation: In the course of an immune response, the binding of ligand (normally the antigenic complex of peptide and MHC receptor complex, TCR-CD3) to the T cell receptor complex on the surface of a T cell initiates changes in the T cell that result in proliferation and/or the expression of cytokines. The tranduction of the signal through the T cell membrane requires the presence of the T cell receptor complex and the associated co-receptors, CD4 and CD8.

Therapeutically effective dose: a dose sufficient to prevent advancement, or to cause regression of a disease, or which is capable of relieving symptoms caused by a disease.

The present invention involves an immunosuppressive composition and a method of using that composition to specifically reduce an APC mediated immune response, including reducing the immune response of a subject or of immune cells ex vivo. These methods expand upon the experimental observation that exposure to GCS not only reduced T cell responsiveness, but that this unresponsiveness was due to alterations at the APC level. In particular, monocytes exposed to the factor have increased IL-10 expression and decreased IL-12, MHC class II and CD80/86 expression and represent a primary cellular defect in glioma-associated immune dysfunction. Thus, these monocytes may serve as the in vivo intermediary between the immunosuppressive factor(s) produced by the tumor cells and the T cells that are affected. The GCS-induced changes in monocytes are those that initiate signals essential for T cell activation. This fact is supported by the demonstration that exposure of monocytes to GCS prior to mixing with autologous T cells and antigen abolished proliferative responses. The changes in monocyte IL-12, IL-10, MHC class II and/or CD80/86 expression therefore affected T cell function.

Previous work has suggested that the immunosuppressive effect of glioma culture supernatant results from the presence of TGF-β in the supernatant (Wrann et al., 1987 and Bodmer et al. 1989). However, the mAb inhibition and immunoprecipitation data of Example 3 demonstrate that TGF-β is not the factor responsible for immunosuppression in the presently disclosed methods. The observed rapid shifts in IL-12 and IL-10 expression/production, and down-regulation of MHC class II and CD80/86, were not due to TGF-β, IL-6, CGRP or a combination of these immunoregulatory molecules.

The presently claimed immunosuppressive composition, which includes one or more glioma-generated factors, appears to include at least one factor that is a protein that has a minimum molecular weight of approximately 40 kD. This would also eliminate TGF-β, as the responsible factor, as it has a molecular weight of about 25 kD). Although the factors in GCS could be known immunoregulatory molecules, elimination of many of the known molecules (see Example 3 below) makes it likely there is at least one new immune modulator that affects monokine expression in the composition. For example adenocarcinoma associated MUC1 mucin inhibits T cell proliferation that is reversible by IL-2 (Agrawal et al., 1998), but addition of rIL-2 to the GCS-treated culture did not restore T cell function (data not shown). Additionally, investigation has shown that the GCS factor is not M-CSF. MCSF was added to 24 hour cultures of human monocytes and no changes in IL-12, IL-10, MHC class II expression or CD80/86 expression were observed (Zou et al., 1998, and unpublished results).

GCS for use in the present invention can be prepared from any known glioblastoma cell line, although variation in the immunosuppressive strength of the resulting preparation is expected. (See Table I). A nonlimiting list of suitable cell lines include SNB 19 (DSMZ no. ACC 325), U251, T98G (ATCC no. CRL-1690), DBTRG-05MG (ATCC no. CRL-2020), M059K (ATCC no. CRL 2365), M059J (ATCC no. CRL-2366), U118 MG (ATCC no. HTB-15), A172 (ATCC no. CRL-1620), A1207, A1235, A2781, U87 MG (ATCC no. HTB-14), U138 MG (ATCC no. HTB-16), and U373 MG (ECACC no. 89081403).

TABLE I

Comparison of effects of culture supernatants from different glioblastoma lines on cytokine production and T cell proliferation by healthy donor PBMC

| PBMC with: | Cytokine production of SAC-stimulated PBMC (pg/ml) | | | PHA-stimulated PBMC |
|---|---|---|---|---|
| | IL-12 (p70) | IL-10 | IFN-γ | $^3$H-TdR up take (cpm) |
| No GCS | 64.9 | 540.4 | 9649.0 | 63917.0 |
| SNB-19[a] | 1.4 | 1337.2 | 483.4 | 2683.0 |
| SNB-19[b] | 14.3 | 1724.8 | 3514.8 | 16321.2 |
| U251[c] | 6.2 | 1497.5 | 2292.6 | 6549.8 |

A representative experiment from 10 or more experiments performed.
[a]Concentrated SNB-19 supernatant from the University of Kentucky laboratory, final dilution of 1:20.
[b]Unconcentrated SNB-19 supernatant from the NCI laboratory, final dilution of 1:2.
[c]Unconcentrated U251 supernatant, final dilution of 1:2.

In specifically disclosed examples, supernatants are harvested from all the glioblastoma lines after 4–7 days of culture and can be concentrated, if desired. The supernatant is stored at −80° C. dilution. In most experiments, GCS preparations were used at a final 1:20 dilution. Table II summarizes the characteristics of the immunosuppressive composition of the present invention.

TABLE II

Partial characterization of GCS activity

| | Test for GCS functional activity | |
|---|---|---|
| Treatment of GCS | Changes in Cytokines | Inhibition of PHA prolifer |
| 56° C. for 30 min | 80–100%* | 0–10%* |
| 100° C. for 30 min | 0–10% | 10–39% |
| pH 2 for 15 min | 40–59% | 60–79% |
| pH 11 for 15 min | 10–39 | 60–79% |
| Trypsin for 30 min | 0–10% | 0–10% |
| Bind to anion exchange column | Yes | Yes |
| Bind to cation exchange column | No | No |
| Gel filtration fraction < 40 kD | 0–10% | 0–10% |
| Gel filtration fraction ≈ 45 kD | 80–100% | 40–59% |
| Gel filtration fraction ≈ 68 kD | 80–100% | 40–59% |
| Gel filtration fraction ≈ 150 kD | 80–100% | 40–59% |

GCS from U251 glioblastoma grown in protein-free media.
*Indicates percent of activity compared to untreated GCS.

The APCs used in the present method can be monocytes or dendritic cells, but monocytes are a desirable type of cell because of ease of collection and isolation. If the cells used are monocytes, obtaining a population would involve drawing sufficient blood to collect 30–40×10$^6$ cells per anticipated treatment cycle. In general, monocytes comprise 20–40% of the PBMC. Monocytes can be isolated, if desired, using the method described in Example 1, or other well known isolation procedures, such as gradients or isolation reagents. If dendritic cells are used, selection of immature cells from the blood is desirable, and can be expanded in vitro with GM-CSF+IL-4. Methods of isolating and culturing immature dendritic cells are described in Thomson et al., U.S. Pat. No. 5,871,728, and references cited therein. Monocytes can be isolated using well known procedures, such as those described in Zou, et al. *J. Immol.,* Apr. 15, 1999.

The introduction of the treated APCs into the subject can occur using any known administration means, including but not limited to intravenous, subcutaneous, intramuscular, and intraperitoneal administration. Monocytes are most easily administered intravenously. Dosages of the treated APCs range, for example, from 30×10⁶ to 60×10⁶ number of cells in a human. Although one treatment may be sufficient to induce the required inhibition of the subject's immune response, any number of administrations of the treated cells can be given to maximize the inhibition of the unwanted immune response.

The present method contemplates prophylactic administration of the treated APCs in the case of transplantation or predisposition for an autoimmune disease, as well as treatment after signs of transplant rejection or autoimmune disease development. For transplants, administration of the APCs from one month to one week before transplantation is suggested, so that the subject's immune system will have time to become unreactive to the donor's antigens. Administration of treated APCs can also occur both before and after transplantation or diagnosis of autoimmune disease, and treatments can continue until the desired inhibition is achieved and maintained, or continued indefinitely. A pharmaceutically acceptable carrier may also be used with the introduction of APCs according to the present method. When administering the APCs to reduce the immune response to transplanted tissue, APCs isolated from the donor is the suggested source. However, the present invention also contemplates the APC source and the donor being different organisms but histocompatible.

The present method can be used alone to inhibit the unwanted immune response, or can be used in combination with other, more crude and general immunosuppressive agents. Such agents include, but are not limited to, cyclosporine A and tacrolimus FK 506. Such additional immunosuppressive agents are generally administered at the time of transplantation, or to counter symptoms of autoimmune disease. The amount given is well known to practitioners and varies with potency and potential toxicity, as well as considerations concerning the effectiveness of the present method and current health of the subject. When administering additional immunosuppressive drugs with the present method, any dosage form known in the prior art is suitable, including solutions for intravenous, subcutaneous, and intramuscular administration. If oral administration is used, capsule, tablet and emulsion are possible means of administration.

If the present method is used to reduce an unwanted autoimmune response, the APCs are isolated from the subject or another histocompatible APC source. Before administration to the subject, the APCs are exposed one or more times to the autoantigenic protein, most effectively, the autoantigenic peptide, associated with the autoimmune disease. This exposure enriches the APC population with cells presenting antigens that elicit the unwanted immune response. Many peptides of autoantigenic proteins are known, particularly those involved in experimentally induced autoimmune diseases. Further, a general method of screening proteins for autoantigenic peptides, involving testing fragments for ability to induce T cell proliferation, is disclosed in Sharma et al., U.S. Pat. No. 5,468,481. Some autoimmune diseases are characterized by inappropriate response to more than one self protein. For example, subjects suffering from SLE can show autoantibodies to one or more of the following antigens: native DNA, denatured DNA, histones, Sm, U1RNP, Ro(SS-A), La(SSB), Ku, PCNA/cyclin, and Ribosomal RNP (Schumacher, ed., 1993). This group of molecules and proteins will be referred to as nuclear antigens. Thus, in treatment of SLE, the present method would contemplate exposure to one or more of these proteins or nucleic acids in order to enrich the APC population for cells specific for reaction to these proteins. Treatment of multiple sclerosis involves exposure of APCs to myelin basic proteins, and particularly a combination of the MBP antigenic peptide and/or B-crystallin. Treatment of rheumatoid arthritis involves pre-exposure to type II collagen; while treatment of myasthenia gravis includes pre-exposure to acetyl choline receptor. Treatment of insulin dependent diabetes mellitius may include pre-treatment with a combination of islet cell surface proteins and/or insulin.

One of the ultimate aims of the present method is to selectively inhibit the immune response of a subject. The inhibition of the immune response is achieved when the production of T cells and related immune effectors, such as cytokines, is reduced in a subject, as compared to the production of T cells and immune effectors that would be stimulated without the treatment method of the present invention. Inhibition of the immune response also occurs when unwanted signs and symptoms are reduced, such as rejection of transplant tissues and the outward signs and symptoms of this rejection, or reduction of the reaction to autoantigenic proteins and the outward signs of this reaction as seen in autoimmune disease. Reduction of the outward symptoms occurs when any one of the symptoms is lessened as compared to what the signs and symptoms would be without the present treatment method.

The inhibition of the immune response is considered selective if any portion of the reduction is enhanced for the selected antigens, that is, if there is any indication that the immune response to the selected antigens is further inhibited than the reduction in the immune response for all antigens as a group. These indications can be measured at the molecular level, through proliferation measures of a treated subjects' T cells, or through outward symptoms, such as lack of rejection of transplanted tissue (as measured by sustained organ function), but continued ability of the immune system to react normally to other exogenous antigens, or a combination of these methods. For example, in rheumatoid arthritis, an objective reduction in articular pain, trythema and swelling may be seen. For myasthenia gravis, a decrease in motor weakness, ptosis or diplopia, or an increase in amplitude of the compound action potential with repetitial nerve stimulation at 3 or 5 Hz may be observed. For a diabetic, improvement could be measured by a decrease in requirements for exogenous insulin to maintain normoglycemia.

The following examples further illustrate the present invention, but are not limiting. Numerous variations and modifications can be made in the methods and compositions disclosed herein, and such variations and modifications are encompassed within the invention. The present disclosure also extends to combinations and subcombinations of the features mentioned and described herein.

EXAMPLE 1

GCS Inhibited T Cell Proliferation

To demonstrate that the preparations of GCS generated by the SNB-19 glioblastoma cell lines inhibited in vitro T cell responses to a mitogen and recall antigens, PBMC from healthy individuals were stimulated with PHA (FIG. 1A) or with a mixture of influenza A virus (FLU), tetanas toxoid (TT) and candida (CASTA) (FIG. 1B) in the absence or presence of GCS. The results indicate that GCS inhibited proliferative responses to both stimuli in a dose-dependent manner at dilution ranging from 1:20 to 1:20,000. Therefore, the GCS produced by the tumor cell line strongly inhibited T lymphocyte responses to a T cell mitogen and to Th-dependent recall antigens that require intact APC function. As negative controls, we found that culture Supernatants from 3 of 7 tumor lines and the two laboratory-generated EBV-transformed cell lines did not inhibit T cell proliferation or induce changes in IL-12 and IL-10 production when added to PBMC (data not shown).

Isolation of PBMC

Samples of whole blood were provided for in vitro laboratory studies by the Transfusion Medicine Department (NIH, Bethesda, Md.), under an NIH IRB-approved protocol. The PBMC were separated on Lymphocyte Separation Media (Organon Teknika, Rockville, Md.), and resuspended at $1.5 \times 10^6$ cells/ml in RPMI-1640 (GIBCO BRL, Rockville, Md.), supplemented with 100 U/ml penicillin, 100 $\mu$/ml streptomycin, 5 $\mu$M HEPES buffer, and 2 $\mu$M glutamine (NIH Media Unit, Bethesda, Md.) and 5% human $AB^+$ serum (Sigma Chemical Co., St. Louis, Mo.).

Production of GCS

The SNB-19 and U251 glioma cell lines were used for production of GCS. Two independently-carried SNB-19 lines were studied: Both originated from Dr. Paul Kornblith (University of Pittsburgh, Pittsburgh, Pa.). One has been available for several years from the University of Kentucky laboratory; the other was recently obtained as a cryopreseved sample from American Type Culture Collection (ATCC Number CRL2219, ATCC, Manassas, Va.). The U251 line (de Ridder et al., 1987) is available in the NCI laboratory. These cells were maintained in RPMI-1640 culture media containing 5% FCS 100U/ml penicillin, 100 $\mu$/ml streptomycin and 10 $\mu$M Hepes buffer in a humidified, 37° C., 5% $CO_2$ incubator. Cells were passaged at 4–7 days intervals using 0.25% trypsin (GIBCO, Grand Island, N.Y.) in PBS pH 7.3–7.4). Supernatants were harvested from all the glioblastoma lines after 4–7 days of culture in 5% FCS RPMI-1640 medium. GCS was also generated by culture the U251 cell line for 3 days in conditioned Cellgro Complete Serum Free Media (Media Inc., Herndon, Va.) or FCS-fee RPMI-1640 to obtain GCS samples for factor purification studies.

Culture supernatants of these glioblastoma lines were rested directly for factor activity by production of IL-12, IL-10, IFN-$\gamma$ and T cell proliferation (see below). Supernatants from one of the SNB-19 cell lines grown to confluency were concentrated (38-to89-fold) on a Minitan tangential flow concentrator using a 100 kD molecular weight cutoff, low protein binding, and regenerated cellulose filters to collect GCS. Following concentration, the GCS was filtered through 0.22 $\mu$m filters (Costar, Cambridge, Mass.) and stored at $-80°$ C. until needed. In most experiments GCS preparations were used at a final 1:20 dilution. Supernatants from the other SNB-19 and the U251 cell lines were either concentrated 20–40 fold using a differential molecular weight cutoff Centricon Plus-80 Centrifugal Filter Device (Millipore, Bedford, Mass.), or were tested without concentration. Culture supernatants exhibited activity, irrespective of whether they had been concentrated. It was verified that different preparations of GCS do not exert a toxic effect on PBMC cultured for 7 days. As controls for the glioblastoma lines, supernatants were tested from ovarian carcinoma A2780, A2780/CP (Behrens et al., 1987) and NIH-ovcar-3, the T2, U937 and K562 lymphoma lines, the prostate carcinoma PC-3 (NIH-ovcar-3, T2, U973, K562 and PC-3 were obtained from ATCC) and two EBV-transformed lymphoma cell lines.

T cell Function Assay

Different preparations of GCS were tested for inhibition of T cell function by culturing $1.5 \times 10^6$ PBMC/ml, or $1 \times 10^6$ T cells/ml with $0.5 \times 10^6$ autologous monocytes/ml in 200 $\mu$l of culture media in 96-well flat-bottom culture plates (Costar) in a humidified, 37° C. 7% $CO_2$ incubator. The cultures were either unstimulated, or were stimulated with PHA-M (1:80 dilution) (GIBCO) or with a pool of recall antigens consisting of: influenza A virus (FLU) (A/Bangkok/RX173, H3N2) (final dilution of 1:800); tetanus toxoid (TT) (Connaught Laboratories, Swiftwater, Pa.) (final dilution of 1:800); and *C. albicans* antigen (CASTA) (Greer Laboratories, Lenoir, N.C.) (10 $\mu$g/ml). The cultures were pulsed with $^3$H-thymidine on day 2 for PHA and day 6 for recall antigens, harvested 20 hours later using a Basic 96 Harvester (Skatron Instruments Inc., Sterling, Va.), and counted in a $\beta$-spectrometer (Wallace Inc., Gaithersburg, Md.).

Enrichment of Monocytes and T cells

Enriched monocytes and T cells were obtained from elutriated lymphocyte-depleted and monocyte-depleted populations isolated from PBMC of healthy blood donors. Remixing experiments were performed using autologous depleted and enriched cell populations.

To obtain enriched monocytes, lymphocyte-depleted PBMC (peripheral blood mononuclear cells) were incubated on ice for 30 minutes with an antibody mixture consisting of mouse anti-human CD3, CD16, and CD19 mAb (IgG) (PharMingen, San Diego, Calif.), at 5 g of each mAb per $10 \times 10^6$ cells in 100 1 PBS containing 10% FBS (PBS/FBS). The cells were washed three times in PBS/FBS, the cell pellet was resuspended in PBS/FBS in the presence of Dynabeads M280 sheep anti-mouse IgG (Dynal, Oslo, Norway)(10 beads/cell), and the mixture was incubated on ice for 30 minutes. The cell-bead mixture was exposed to a magnet through three cycles of magic separation and washing of the unattached cells. This procedure resulted in enrichment of monocytes to greater than 90% $CD14^+$ cells, determined by flow cytometry. The enriched monocytes were tested by flow cytometry for the presence of $CD83^+$ cells, a marker of mature dendritic cells, and none were detected.

To obtain enriched T cells, monocyte-depleted cells were incubated with the Lympho-Kwik-T Isolation Reagent (One Lambda, Canoga Park, Calif.), which depletes of all cell types except T cells by antibody mediated, complement-dependent lysis.

EXAMPLE 2

Figure 2:
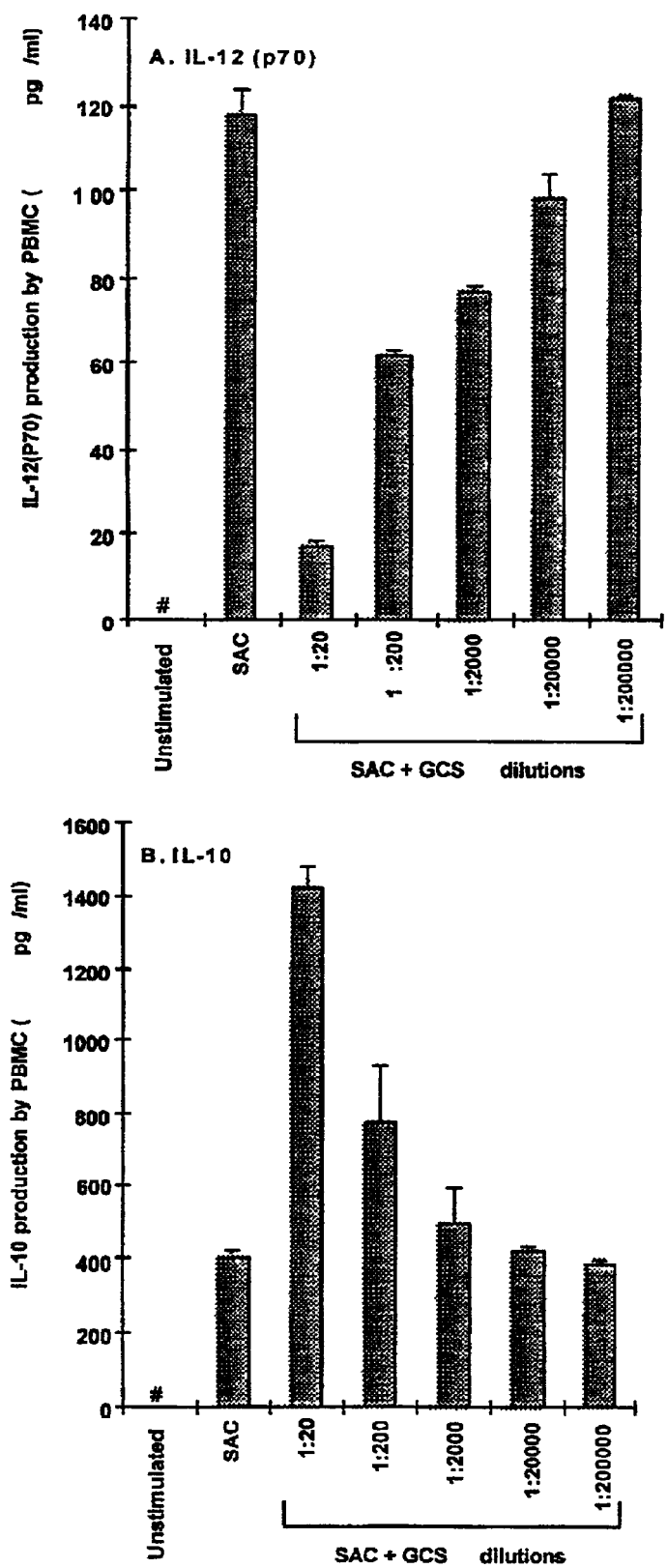
FIG. 2A is a graph showing that GCS affects SAC-stimulated IL-12 production by PBMC in a dose dependent manner. Stimulation was present for 24 hours. Production of IL-12 was measured by ELISA.
FIG. 2B is a graph showing GCS affecting S. aureus Cowan strain 1 (SAC)-stimulated L-10 production by PBMC in a dose-dependent manner. Stimulation was present for 24 hours. Production of IL-10 was measured by ELISA. Two experiments were performed with PBMC from two donors each (n=2), and the results shown are from one representative experiment. The symbol # indicates that IL-10 production was below a detectable level.

GCS Decreased Production of IL-12 and Increased Production of IL-10 in PBMC, Isolated Monocytes, and A Mixed Monocyte/Autologous T-Cell Population Because SAC is a strong stimulator of IL-12 and IL10 production by monocytes, the production of these interleukins was assayed in varying dilutions of GCS in 24 hour cultures of SAC-stimulated PBMC. The data in FIG. 2 demonstrate that GCS decreased IL-12 and increased IL-10 production in a dose-dependent manner.

Figure 3:
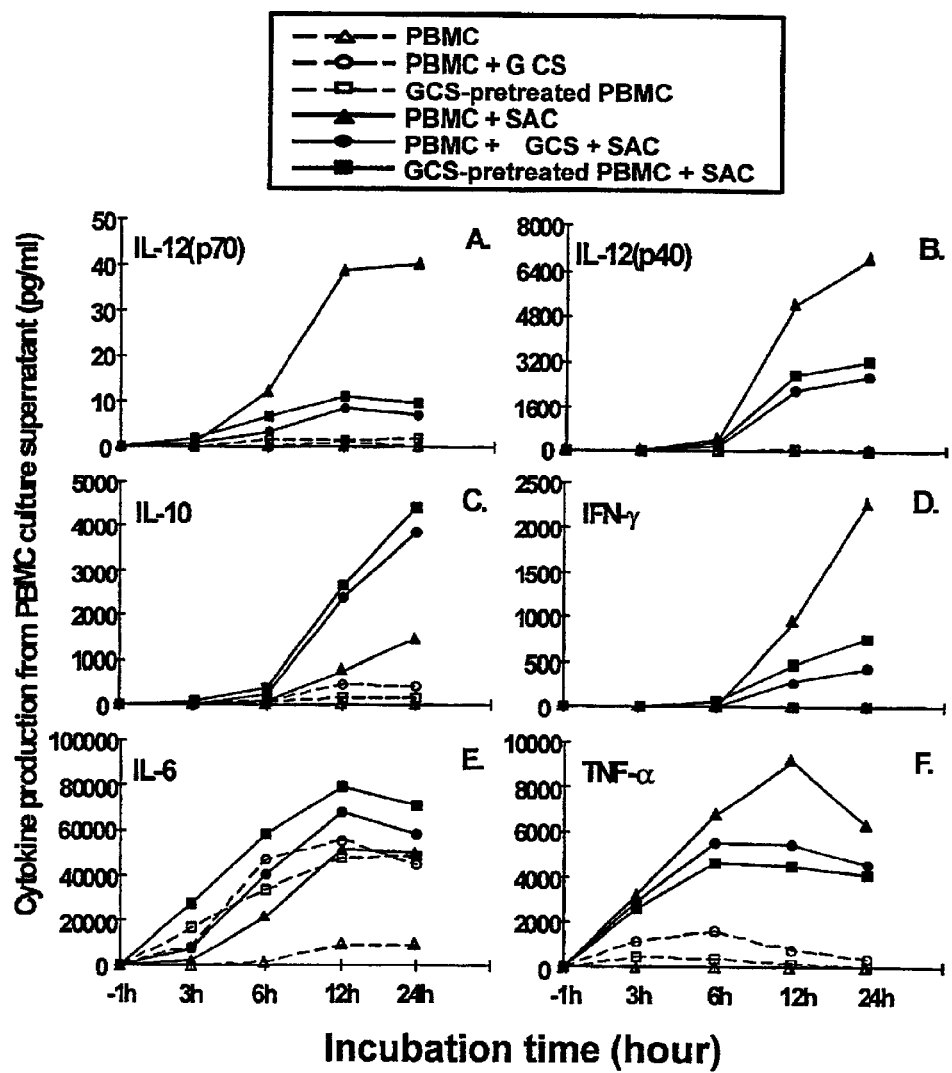
FIG. 3 shows that GCS can rapidly induce cytokine production changes in SAC-stimulated PBMC. The effect of SAC and/or GCS on the kinetics of production of the cytokines is indicated in the panels. Panel A shows production of IL-12 p70, panel B shows production of IL-12 p40, panel C shows production of IL 10, panel D shows proton of IFN-$\gamma$, panel E shows production of IL-6, and panel F shows production of TNF-$\alpha$. The x-axis point "-1h" indicates the group that was pre-incubated with GCS for 1 hour before washout and stimulation with SAC. GCS were used as final 1:20 dilution. Two experiments were performed with PBMC from two donors each (n=2), and the results shown are from one representative experiment.

To determine the kinetics of cytokine production, GCS was added to PBMC at the time of SAC stimulation, and the cultures were carried for 3, 6, 12 arid 24 hours. In addition to IL-12 and IL-10, we tested for other SAC-stimulated monokines and cytokines, including IFN-$\gamma$, IL-6 and TNF-$\alpha$. PBMC were also preincubated with GCS for 1 hour, the GCS was washed out, and the treated PBMCs were stimulated with SAC for 3, 6, 12 and 24 hours (FIG. 3). The cytokine production of control cultures not incubated with GCS, was also measured in cells that were stimulated or not stimulated with SAC. The production of IL-12 p70 and p40, as well as IFN-$\gamma$, were greatly reduced by addition of GCS to SAC-stimulated PBMC (panels A, B and D). In contrast, GCS increased SAC-stimulated IL-10 production panel C). IL-6 production was appreciably increased by GCS or SAC alone, and the combination of GCS and SAC induced an additional increase (panel E). SAC-stimulated TNF-α production was reduced approximately 2-fold by GCS (panel F). Data similar to those shown in FIG. 3 were obtained in six independent experiments. We also observed that 48 hour cultures of GCS and SAC yielded results indistinguishable for the 24 hour cultures (data not shown). These results indicate that GCS can rapidly induce a decrease in the production of IL-12 and IFN-γ, and a concomitant increase in IL-6 and IL-10 production. The one hour preincubation of PBMC with GCS prior to SAC stimulation induced changes in cytokine profiles that were similar to those observed when PBMC were exposed to GCS and SAC simultaneously.

Culture supernatants generated by the two SNB-19 glioblastoma lines as well as by the U251 glioblastoma line all induced decreased IL-12 and IFN-γ, increased IL-10 production, and also abolished PHA-stimulated T cell proliferation (Table I). Culture supernatants from 4 of 7 control tumor cell lines exhibited weak GCS-like activity (A2780, NIH-ovcar-3, T2, PC-3). As noted above, supernatants from the three other tumor lines did not show any GCS-like activity (A2780/CP, U937, K562).

The results of additional kinetic experiments in which GCS was preincubated with PBMC for different time intervals prior to SAC stimulation are summarized in Table III. Incubation of GCS with PBMC for as little as 3 minutes resulted in decreased Il12 p40 and IFNγ and increased IL-10 production in SAC-stimulated cells. Preincubation with GCS for one hour was as effective in altering the SAC induced response as maintaining GCS in the cultures win SAC for 24 hours.

13.0% stained for IL-10, 1.9% stained for IL-12 and 1.6% stained for both cytokines. Similar results were obtained in four repetitive experiments. In contrast to the cells gated for lymphocytes, no T cells were found that produced IL-10 or IL-12 after a 24 hours incubation with GCS, SAC, or SAC+GCS (data not shown).

Effect of GCS on Enriched SAC-stimulated Monocytes

Figure 4:
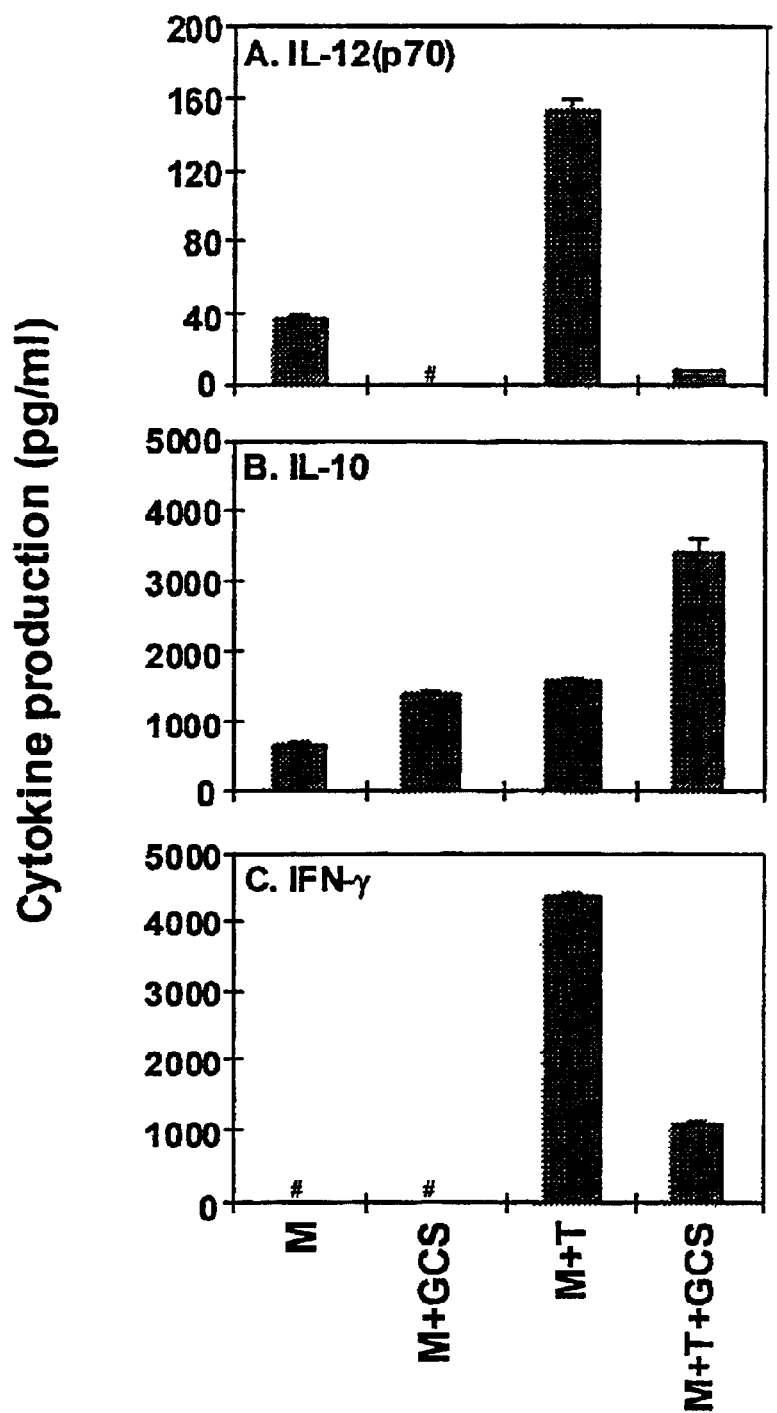
FIG. 4 shows the presence of T cells affecting IL-12 and IL-10 production by monocytes. Production of IL-12 p70 (A), IL-10 (B) and IFN-$\gamma$ (C) by SAC-stimulated monocytes with/without T cells is shown for the following cell populations: monocytes (M); monocytes+GCS (M+GCS); monocytes+T cells (M+T); and monocytes+T cells+GCS (M+T+GCS). Four experiments were performed with PBMC from four donors each (n=2), and the results shown are from one representative experiment. The symbol # indicates IL production was below a detectable level.

To determine whether incubation with GCS also affected IL-12 p70, p40 and IL-10 produced by enriched monocytes, the following experiments were performed. Monocytes were enriched from PBMC by elutriation followed by negative selection of T, B and NK cells. The enriched monocytes (shown>90% CD14+, but undetectable (<1%) for CD3+, CD19+, CD1a+ and CD16+) were stimulated with SAC for 24 hours in the absence or presence of GCS. The results (labled M+GCS in FIG. 4) indicate that GCS abrogated IL-12 production (FIG. 4A) and increased IL-10 production (FIG. 4B). GCS also decreased SAC-stimulated IL-12 p40 production by 2-fold (data not shown). These results indicate that GCS can also affect IL-12 and IL-10 production by enriched monocytes in the absence of other cell types.

To determine whether T cells would affect SAC- and GCS-regulated monokine production, isolated autologous T cells (>95% CD3+) were added to SAC-stimulated monocytes. The T cells enhanced IL-12 four-fold (M+T in FIG. 4), but addition of GCS (M+T+GCS) greatly reduced IL-12 production (FIG. 4A). Addition of autologous T cells (M+T) increased IL-10 production by 2-fold above monocytes alone (M), and addition of GCS M+T+GCS) further increased IL-10 production (FIG. 4B). SAC-stimulated IFN-γ production was also assessed in the same cultres (FIG. 4C), and demonstrated that without T cells, this cytokine was not produced. Addition of T cells (M+T) resulted in

TABLE III

Effect of incubation of PBMC with GCS for different time intervals on SAC-stimulated IL-12, IL-10 and IFNγ production

| PBMC were pre-incubated in 37° C. for total 1 hour | Content of 24 hours cultured | IL-12(p70) | IL-12(p40) | IL-10 | IFNγ |
|---|---|---|---|---|---|
| PBMC | SAC | 34.3 ± 8.6 | 4870 ± 476 | 932 ± 189 | 3327 ± 719 |
| PBMC | SAC + GCS | ↓[a] > 10[c] | ↓3.4 ± 0.3 | ↑[b]2.2 ± 0.2 | ↓4.2 ± 0.5 |
| Pre-incubation with GCS for 1 hour | SAC | ↓ > 10[c] | ↓3.6 ± 0.2 | ↑3.5 ± 0.6 | ↓5.9 ± 1.1 |
| Pre-incubation with GCS for 15–30 minutes | SAC | ↓ > 10[c] | ↓3.4 ± 0.3 | ↑3.0 ± 0.4 | ↓3.3 ± 0.5 |
| Pre-incubation with GCS for 3–10 minutes | SAC | ↓6.3 ± 1.1 | ↓1.8 ± 0.1 | ↑2.5 ± 0.2 | ↓2.8 ± 0.4 |

[a,b]The fold increase (↑) or fold decrease (↓) change from SAC-stimulated PBMC based on the mean of four independent experiments (SEM).
[c]Below detectable level. GCS was used at final dilution of 1:20 in the culture and pre-incubation system To determine whether moncytes contained in the PBMC were responsible for the production of IL-12 and IL-10, 24 hour SAC-stimulated PBMC were gated for CD14+ and CD3+ cells and stained with anti-IL-12 and anti-IL-10 antibodies. IL-12 and IL-10 were detected only in the CD14+ population. PBMC incubated alone or with GCS, SAC or SAC+GCS were used for isotype control staining (data not shown). Immunostaining data indicated that 3.4% of the monocytes stained for intracellular IL-10, but only 0.3% stained for IL-12. Stimulation of PBMC with SAC alone resulted in the staining of 8.1% for IL-10, 5.7% for IL-12 and 1.5% for both. The PBMC incubated with SAC+GCS resulted in a skewing toward IL-10 producing cells, as IFN-γ production, which was reduced approximately 4-fold by GCS (M+T+GCS).

Figure 5:
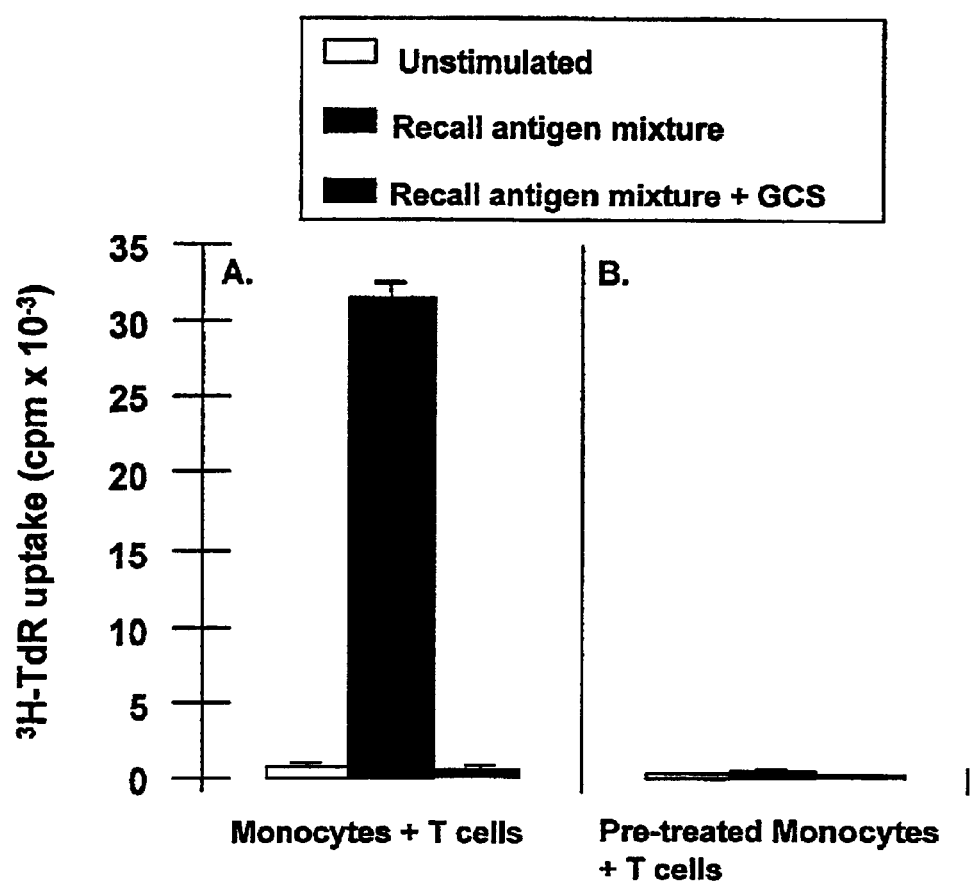
FIG. 5 is a graph showing that GCS pre-treated monocytes lost APC function in the recall antigen induce T cell proliferative response. Recall antigen pool-stimulated T cells proliferation with autologous monocytes in the absence or presence of GCS (A); T cells with GCS-pre-treated monocytes (after preincubation with GCS for 1 hour) in the absence or presence of GCS (B). Three experiments were performed with purified T cells and autologous purified monocytes from four donors each (n=3), and the results shown are from one representative experiment.

To determine whether the observed GCS-induced changes in monokine production would be reflected in T helper cell function, a mixture of autologous monocytes and T cells were stimulated with the recall antigen mixture of FLU, TT and CASTA, and thymidine incorporation measured 6 days later. Similar to the data obtained for IL-12 and IL-10 production, addition of GCS to cultures of monocytes during antigen stimulation, or preincubation of monocytes with GCS for one hour prior to mixing with T cells and antigen stimulation, abrogated the antigen sated proliferative response (FIG. 5).

Cytokine Production and Detection

In general, the production of cytokines by PBMC, enriched monocytes, or monocytes plus autologous T cells were assessed by culture media $3 \times 10^6$ PBMC, $1 \times 10^6$ monocytes, or $1 \times 10^6$ monocytes plus $2 \times 10^6$ T cells in 2 ml of culture media in 24-well plates (Costar), respectively, in a humidified, 37° C. 7% $CO_2$ incubator. Cells were either unstimulated or were stimulated with *S. aureus* Cowan strain 1 (SAC) (0.01%) (Pansorbin, Calbiochem-Behring Corp., La Jolla, Calif.). Culture supernatants were harvested after 24 hours and stored at −80° C.

The IL-12 p70 heterodimer production was assessed by ELISA from R&D (Minneapolis, Minn.). Total IL-12 p40, IL-2, IL-4 and IL-6 productions were detected by ELISA from Genzyme (Cambridge, Mass.). IL-10, IL-5, IFN-γ and TNF-α productions were assessed in the supernatant of cultures stimulated with SAC-stimulated for 24 hours using Pharmingen capture and detection antibodies as previously described (Clerici et al., 1994). The limit for detection of these cytokines was in the range of 5–20 pg/ml.

Detection of Intracellular Cytokines

PBMCs were cultured for 6 hours with or without stimulation in Teflon vials Pierce Chemicals, Rockford, Ill.) in a 37° C., 7% $CO_2$ incubator, then Brefeldin A (Sigma Chemicals, St. Louis, Mo.) (5 μg/ml) was added for an additional 18 hours of incubation. In some experiments PBMC were cultured without or with 10 μg/ml Brefedin A in 5% human $AB^+$ serum RPMI-1640 medium for 1 day. Cell viability was tested by Trypan Blue exclusion or PI staining. The cells also were analyzed by FACS with anti-CD3 and CD14 staining. No differences were obtained in cell viability (>90%) in either the $CD3^+$ or $CD14^+$ populations in the presence or absence of Brefeldin A. Cells were harvested and washed in a staining buffer (PBS containing 1% FBS and 0.1% w/v sodium azide), preincubated with human IgG at 4° C. for 30 minutes to block FcR. The cells were then stained at 4° C. for 30 minutes with fluorochrome-conjugated mAb specific for a cell surface antigen such as CD14 and CD3 (Pharmingen, San Diego, Calif.). The cells were subsequently washed with staining buffer, pelleted by centrifugation and fixed in 500 1 of fixing buffer (4% w/v paraformaldehyde in PBS) at 4° C. for 30 minutes or overnight. The cells were washed in the staining buffer, pelleted by centrifugation and resuspended in 100 μl of permeabilization buffer (PBS containing 1% FBS, 0.1% w/v sodium azide, 0.1% w/v saponin). The cells were incubated for 30 mimes at 4° C. with 0.5 g fluorochrome-conjugated anti-cytokine antibodies (anti-IL-12 p40 and p70, IL-10, IL-6, , INF-γ and TNF-α from Pharmingen), washed twice in permeabilization buffer, resuspended in staining buffer and analyzed by flow cytometry using a FACScan (Becton-Dickinson, San Jose, Calif.). The cells were gated on monocytes or lymphocytes based on forward and side light scatter. In some experiments the binding of fluorochrome-conjugated anti-cytokine mAb was blocked by preincubation of the conjugated mAb with excess recombinant cytokine IL-12 p40 and IL-10, Pharmingen).

EXAMPLE 3

The Immunosuppressive Effects of GCS are Not Traceable to a Large Battery of Known Factors To identify immunoregulatory factors that might be contained in GCS, six different lots of supernatants were collected from one of the SNB-19 glioblastoma cell line that had been shown to inhibit in vitro T cell proliferation. The supernatants were found to contain IL-6, TGF-β1, calcitonin gene-related peptide (CGRP) (Fox et al., 1997) and very low levels (below 7 pg/ml) of prostaglandin-E2 (PGE2) (Table IV), but not detectable levels of IL-4, IL-10, IL-12, TNF-α or IFN-γ (data not shown). The levels of PGB2 detected were below those reported to reduce IL-12 production by human PBMC or dendritic cells (van der Pouw Krann et al., 1995, and Kalinski et al., 1997). Based on these data, three types of experiments were performed to determine whether the changes in cytokine production induced by GCS could be attributed to any of these immunosuppressive factors.

TABLE IV

Immunosuppressive molecules detected in six different preparations of undiluted GCS

| GCS Lot. Activity Estimate[a] | IL-6 (pg/ml) | TGF-β1 (pg/ml) (Active form) | CGRP (pg/ml) | $PGR_2$ (pg/ml) |
|---|---|---|---|---|
| A ++++[b] | 1367 | ND | ND | ND |
| B + | 1689 | 706 | 5700 | <7 |
| C ++++ | 533 | 850 | 8300 | <7 |
| D ++ | 626 | 812 | 4600 | 0 |
| E +++ | 253 | 564 | 15500 | <7 |
| F ++++ | 1392 | ND | 27600 | <7 |

Cytokines that were set detected in GCS were IL-2, IL-4, IL-5, IL-10, IL-12, TNF-α and IFN-γ
[a]Activity of different GCS preparations were compared for modulation of IL-12, IL-10 and IFN-γ production by PBMC.
[b]++++ and + indicate GCS preparations that had the greatest and least effects, respectively on changing IL-12, IL-10 and IFN-γ

First, it was determined whether the addition of exogenous IL-62, TGF-α1, TGF-β2, or CGRP to PBMC, either singly or in combination, would decrease IL-12 and/or IL-10 production. IL-6 (10 ng/ml-to 10 pg/ml), TGF-β1 or TGF-β2 (10 ng/ml-to-10 pg/ml), or CGRP (1 μg-to-10 pg) was added to SAC-stimulated PBMC, as well as the combination of IL-6 (5 ng/ml), TGF-β1 (1 ng/ml), TGP-β2 (1 ng/ml) and CGRP (50 ng/ml). Under none of the above conditions were changes detected in IL-12 or IL-10 production (data not shown). Second, treat of GCS with neutralizing Abs against IL-6 and CGRP and TGF-β1,-β2 and -β3 had no effect on its ability to decrease IL-12 and IFN-γ production and to increase IL-10 production by PBMC. Third, IL-6, TGF-β and CGRP were immunoprecipitated, either singly or in combination, with the same Abs used for inhibition. The GCS treated in this way did not lose any of its ability to decrease IL-12 production. Only slight reductions were observed in ability to increase IL-10 and decrease IFNγ by combination immunoprecipitation of IL-6 and TGF-β (Table V). Taken together, these results do not support the conclusion that the cytokine dysregulation induced by GCS is the result of IL-6, TGF-β or CGRP, acting singly or in combination.

TABLE V

Removed of IL-6, TGF-β and CGRP by immunoprecipitation had no effect on the ability of GCS to alter IL-12 and I cytokine profiles of PBMC

| PBMC | Culture without/with immunoprecipitated $GCS^a$ (final 1:40) | Cytokines determination by ELISA (pg/ml) | | |
|---|---|---|---|---|
| | | IL-12 (p40) | IL-10 | IFN-γ |
| Unstimulated | — | 0 | 5 | 0 |
| SAC | — | 3372 | 1339 | 1120 |
| SAC | GCS (none Ab) | 1263 | 3104 | 78 |
| SAC | GCS (anti-IL-6) | 1283 | 2920 | 73 |
| SAC | GCS (anti-TGF-β) | 1092 | 3072 | 137 |
| SAC | GCS (anti-CGRP) | 1075 | 3017 | 98 |

TABLE V-continued

Removed of IL-6, TGF-β and CGRP by immunoprecipitation had no effect on the ability of GCS to alter IL-12 and I cytokine profiles of PBMC

| PBMC | Culture without/with immunoprecipitated GCS[a] (final 1:40) | Cytokines determination by ELISA (pg/ml) | | |
|---|---|---|---|---|
| | | IL-12 (p40) | IL-10 | IFN-γ |
| SAC | GCS (anti-IL-6 & TGF-β) | 1256 | 2678 | 225 |
| SAC | GCS (anti-IL-6, TGF-β & CGRP) | 1296 | 2496 | 209 |

[a]The experimental procedure is shown in the Material and Methods.

Ion Exchange and Gel Filtration Columns

The supernatants were harvested from the U251 glioblastoma line after 3 days of culture in conditioned FCS-free RPMI-1640 media. The GCS samples for factor purification sties were tested for binding to CM, Q, SP and DEAE Sepharose Fast Flow Columns Pharmacia Biotech). The unbound fraction and eluted fractions were tested for GCS activity. The bound fractions that contained GCS activity were fractionated on the Superdex 75 and Superdex 200 columns (Pharmacia Biotech). To determine the m.w. of the active factor(s), 25-to-50 fractions were each tested for GCS activity by analysis of IL-12, IL-10, IFN-γ production and PHA-stimulation response of PBMC, and compared with the unfractionated GCS, as described above.

Immunoprecipitation

To remove IL-6, TGF-β and CGRP, GCS was diluted 7-fold in PBS. Anti-IL6 (clone MQ2-13A5 rat IgG1, final concentration of 5 µg/ml), anti-TGF-β mAb (mouse IgG1, final concentration of 10 µg/ml) and rabbit anti-human CGRP serum (final 1:120 dilution) were added singly or in combination. The GCS and Ab mixture was incubated overnight at 4° C. under rotating conditions. An excess of GammaBind G Sepharose (Pharmacia Biotech, Piscataway, N.J.) was added for 10 hours, and the mixture was centrifuged for 10 minutes at 2000 Xg. An excess of Protein A Sepharose (Pharmacia) was added to the supernatant which was incubated overnight under rotating conditions at 4° C. The mixture was centrifuged again and the supernatant was sterilized by passing through a 0.22 µm filter, then tested for ability to suppress the Th function and induce the cytokine changes seen with the original GCS. Specific ELISA or EIA verified that the immunoprecipitation removed all detectable IL-6, TGF-β and CGRP.

Reagents

The additional following reagents were used in this study: anti-human IL-10 neutralizing mAb (clone JES 319 F11, DNAX, Palo Alto, Calif.); anti-human IL-10R mAb (clone 37607.11, R&D); anti-human IL-6 neutralizing mAb (clone MQ2-13A5, Pharmingen); paraformaldehyde and saponin (Sigma Chemicals); transforming growth factor-1 (TGF-1) human ELISA kit and prostaglandin E2 enzyme immunoassay (EIA) kit (Biotrak, Amersham); ultrapure natural TGF-β1, recombinant human TGF-β2 and mouse monoclonal anti-human TGF-β1,-β2,-β3 neutralizing Ab (Genzyme); human calcitonin gene related peptide (CGRP); rabbit anti-human CGRP serum and high sensitivity EIA kit (Pennisula Laboratories Europe, Ltd, Belmont, Calif.); and insoluble trypsin (Sigma Chemicals).

EXAMPLE 4

GCS Reduced MMC II and CD 80/86Expression on Monocyte Surface

To determine whether exposure to GCS would affect expression of MHC class II and CD80/86 (B7.1 and B7.2) expression, PBMC were pre-incubated for one hour with GCS and then incubated with medium in the absence or presence of rIFN-γ for 24 hours (Table VI). The cultured cells were analyzed by flow cytometry by gating on $CD14^+$ population of monocytes to determine class I, class II, CD80 and CD86 expression. The results indicate that MHC class II but not class I expression was reduced by approximately 2-fold. Expression of CD80 and CD86 were similarly reduced. Although rIFN-γ enhanced class I, class I and CD80 expression on monocytes, GCS reduced the mean channel fluorescence increases by approximately 2-fold for class II and CD80, but not for class I.

TABLE VI

GCS down-regulates MHC class II and B7, but does not affect MHC class I expression on monocytes

| Cells | Culture | Mean Channel Fluorescence (MCF) | | | |
|---|---|---|---|---|---|
| | | HLA-DR (MHC class II) | CD80 (B7.1) | CD86 (B7.2) | HLA-A,B,C (MHC class I) |
| PBMC | Media | 572.6 (4.5)[a] | 5.2 (3.4) | 818.0 (4.8) | 1557.1 (5.5) |
| GCS-treated PBMC | Media | 283.9 (4.8) | 5.2 (4.2) | 414.3 (4.4) | 1544.7 (5.5) |
| PBMC | Media + IFN-γ | 2011.8 (18.9) | 30.2 (5.4) | 876.8 (5.1) | 2212.7 (7.1) |
| GCS-treated PBMC | Media + IFN-γ | 895.9 (12.8) | 13.1 (6.1) | 351.6 (6.5) | 2445.3 (7.8) |

PBMC were pre-incubated with/without GCS (final 1:20) at 37° C. for 1 hour, washed twice with medium. 1.5 × 10⁶/ml PBMC were then cultured with/without hIFN-γ 100 U/ml) for 24 hours. Cells were stained with anti-CD14-PE/FITC and gated on CD14 positive monocytes to show difference in MCF of anti-HLA-DR, CD80, CD86, HLA-A,B,C-FITC/PE staining, respectively. The date shown are representative of one of four experiments performed on PBMC from six donors.
[a](..) indicates MCF of the isotype control.

EXAMPLE 5

GCS Increases the Length of Viability of Skin Grafts in Mice

This example illustrates use of the method of the present invention to increase viability of a skin allograpt. Monocytic antigen-presenting cells (APC) from one inbred mouse strain are exposed ex vivo to human glioma culture supernatant (GCS) prior to intravenous (iv) inoculation of the treated cells into an unrelated strain of mouse. The recipient strain is subsequently transplanted with a skin graft from the donor strain, and the time of rejection determined.

Spleen cells are removed from the prospective C57BL/6 ($H-2^b$) donor stain (abbreviated B6), the cells treated for one hour at 37° C. with a 1:20 dilution of GCS, and the cells washed three times with culture media, and inoculated approximately 5×10$^7$ cells iv into the prospective BALB/c (H-2$^d$) recipient strain (abbreviated BALB). At 2-week intervals for up to 6 weeks (initial pilot trial), the recipient mice are grafted with a B6 skin graft on one flank and a C3H (H-2$^k$) skin graft on the other flank (as a negative control). Untreated mice serve as controls for rejection. The allografts are monitored daily until all grafts have been rejected, or up to 150 days, if the treated mice do not exhibit rejection of the B6 allografts. It is expected that the C3H grafts in both groups, as well as the B6 grafts in the untreated mice, are rejected within approximately 2 weeks. At the time of grafting, sample mice from the treated and untreated groups are euthanized, and their spleen cells stimulated in vitro with irradiated B6 and C3H spleen cells to determine whether there is in vitro evidence of T cell unresponsiveness selective for B6 stimulators. The magnitude of this in vitro response is assessed by pulsing the cultures with $^3$H-thymidine to determine antigen-stimulated DNA synthesis, or any other well-known method of assessing in vitro T cell response.

EXAMPLE 6

Prolongation of Graft Survival Using Intra-Peritoneal Injections of GCS

The U251 glioma cell lines were used for production of GCS. GCS was prepared by flushing a CELLMAX Artificial Capillary Cell Culture System (Spectrum Labs, Laguna Hills, Calif.) with 500 ml of PBS before harvesting the GCS from within the Cellmax culture chamber (fitted with 10 KD exclusion filters).

Eight week old BALB/C (H-2$^d$) mice were engrafted on the flank with tail skin graft from eight week old C57 BL/J6 (H-2$^b$) female mice in an adaptation of the method of Billingham and Medwar (J. Exp. Med. 146:2513, 1991). Bandages were removed on day 5 and the graft was scored daily until rejection. Rejection was defined as loss of greater than 80% of the grafted tissue.

The mice were divided into two groups. One group received 0.5 ml of undiluted human GCS, administered i.p. on days −1, 0, 2, 4, 6, 8, 10, and 12. The second group served as a control.

Figure 6:
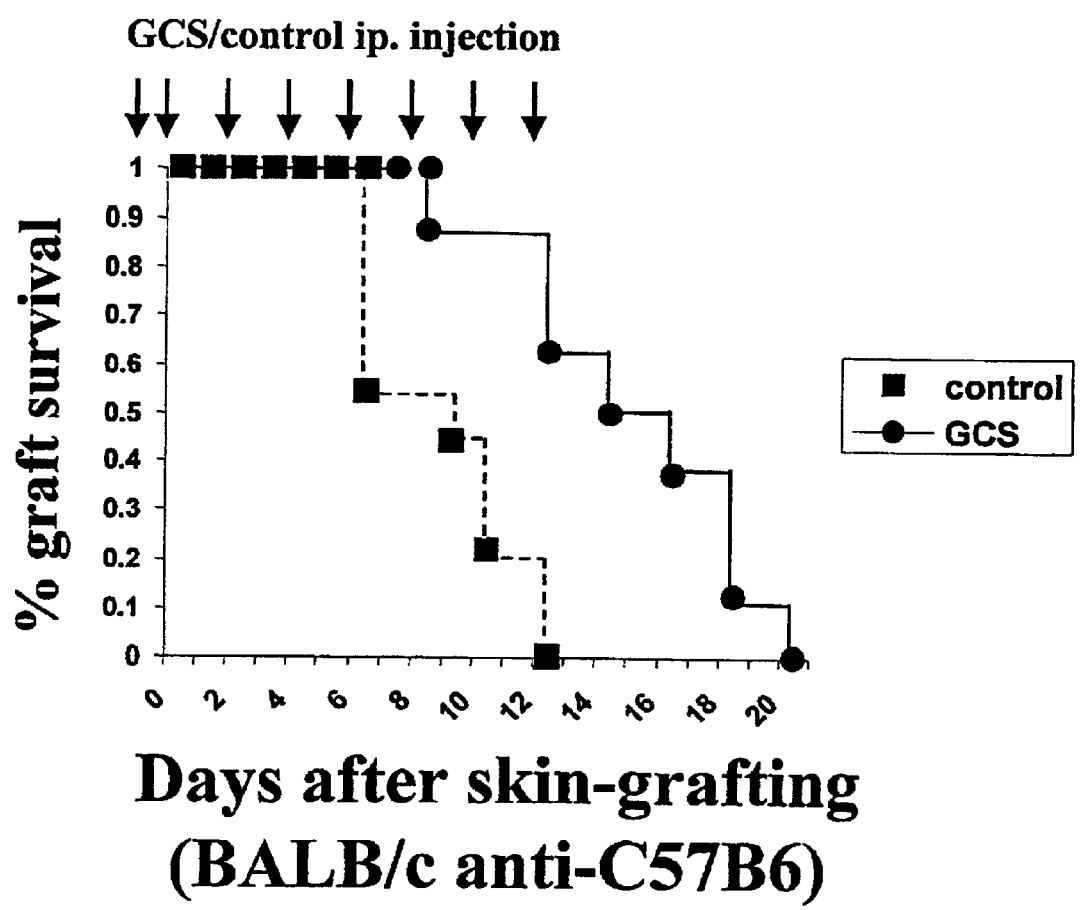
FIG. 6 is a graph illustrating increased graft survival induced by treatment with GCS. Squares indicate % graft survival in control animals, while circles indicate % graft survival with GCS treatment. GCS was prepared by flushing a CELLMAX artificial capillary cell culture system with 500 ml of PBS before harvesting the GCS from within the Cellmax culture that is filtered with 10 KD exclusion filters. Results shown are from one representative experiment.

Results are shown in FIG. 6. Treatment of the graft recipients with GCS resulted in the prolongation of graft survival.

EXAMPLE 7

Reduction of PHA-Induced Stimulation of BALB/c Spleen Cells

To determine if GCS could reduce the stimulation of lymphocytes, the effect of GCS treatment was evaluated in a PHA-induced mouse spleen T cell proliferation assay. Spleens were dissected from Balb/c mice, and the cells were released from the spleen capsule. The spleen cells were then resuspended in complete medium (RPMI-1640 (GIBCO BRL, Rockville, Md.), supplemented with 100 U/ml piclin, 100 $\mu$g/ml streptomycin, 5 $\mu$M HEPES buffer, 2 $\mu$M glutamine, 5×10$^{-5}$ M 2-mercaptoethanol and 10% FCS), and cultured at a concentration of 2.5×10$^5$ cells per culture, in a total volume of 0.2 ml of complete medium.

Each proliferation assay was performed in triplicate in flat microculture plater (Costar, Corning Incorporated, Corning, N.Y.). The plates were maintained in a humidified atmosphere at 7% CO$_2$ at 37° C. for 3 or 4 days in culture.

Figure 7:
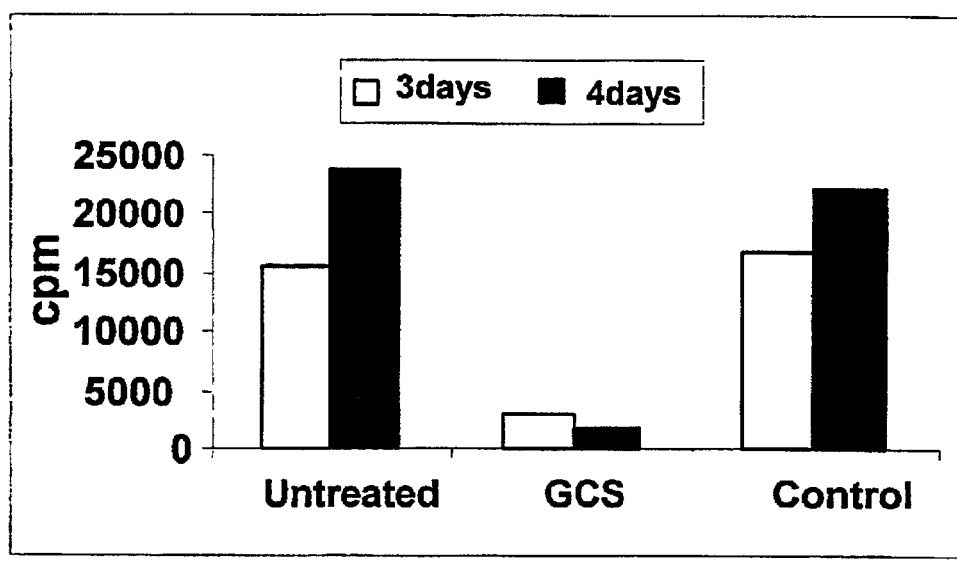
FIG. 7 is a graph showing that GCS pretreatment of BALB/c spleen cells inhibits phytohemagglutinin (PHA) induced proliferation.

BALB/c spleen cells were incubated for 1 hour at 37° C. with GCS (pretreatment) before stimulation for 3 (open bar) or 4 days (filled bar) with the T cells mitogen PHA. The PHA-stimulated cultures were then pulsed with $^3$H-thymidine. Specifically, the cultures were pulsed with 20 KBq/well of $^3$H-thymidine on last 6 hours, harvested by using a Basic 96 Harvester (Skatron Instruments Inc., Sterling, Va.), and counted in a $\beta$-spectrometer (Wallac Inc., Gaithersburg, Md.). FIG. 7 shows the results obtained from one representative experiment (results from cells treated with control media or results from untreated cells are shown for comparison). The results demonstrate that pre-treatment with GCS resulted in a reduction of PHA-stimulated proliferation of BALB/c spleen cells.

EXAMPLE 8

Effect of pre-treatment with GCS on MLR

In order to demonstrate that treatment with GCS affected responder cells and simulator cells, the effects of GCS pre-treatment were evaluated in a mouse mixed lymphocyte reaction (MLR). The responding spleen cells were obtained from a pool of 3 BALB/c mice, as described above. The stimulating spleen cells were similarly obtained from CS7BL/6 (B6) mice.

The BALB/c spleen cells were resuspended in complete medium and cultured at a concentration of 2.5×10$^5$ cells per culture well together with 2.5×10$^5$ gamma-irradiated (3000 rads) stimulating C57B/6 (B6) spleen cells in a total volume of 0.2 ml. Each MLR was performed in triplicate in round microculture plates (Costar, Corning Incorporated, Corning, N.Y.) and maintained in a humidified atmosphere at 7% CO$_2$ at 37° C. The cultures were pulsed with 20 KBq/well of $^3$H-thymidine on day3, harvested 20 hours later using a Basic 96 Harvester (Skatron Instruments Inc., Sterling, Va.), and counted in a $\beta$-spectrometer (Wallac Inc., Gaithersburg, Md.).

Figure 8:
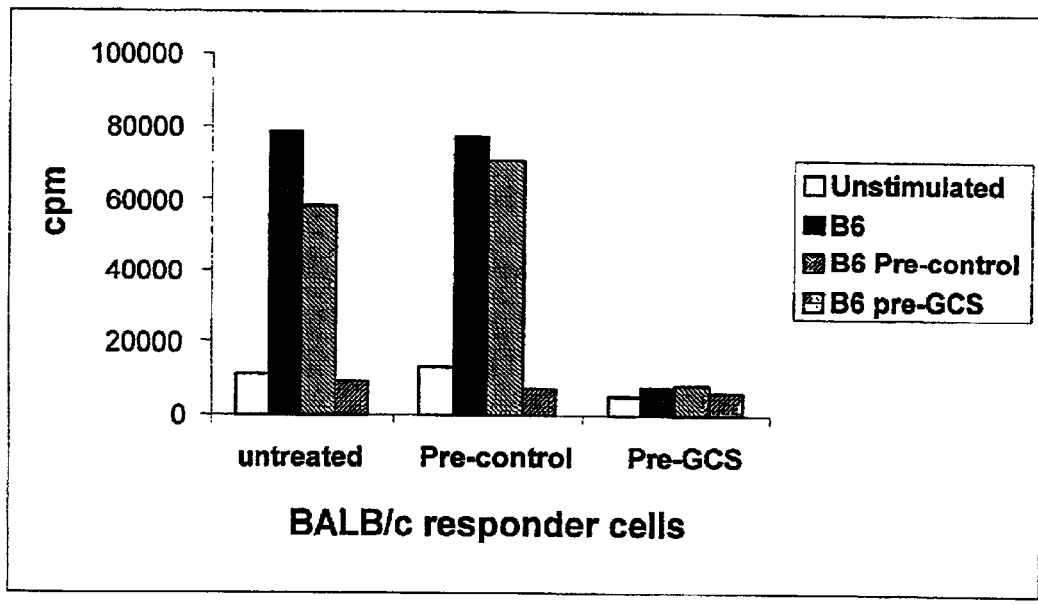
FIG. 8 is is a graph demonstrating that GCS-pretreatment of responder or stimulator cells suppresses a mixed lymphocyte reaction (MLR). Effect of pretreated of irradiated C57BL/6 (B6) stimulators on BALB/c anti-B6 MT. B6 stimulators were pretreated for 1 hour with either a negative control culture supernatant or GCS containing supernatant (see legend). They were then washed and added to BALB/c responder spleen cells. "Untreated" are control cultures where BALB/c responder spleen cells were used directly in a 4-day MLR; "Pre-control" indicates that responder cells were pretreated with a control culture supernatant (no GCS); "Pre-GCS" indicates responder cells were pretreated with GCS. Results shown are from one representative experiment.

The responding spleen cells were divided into three groups: "Untreated" indicates the BALB/c responding spleen cells were used directly; "Pre-control" indicates the BALB/c responding cells were pretreat for 1 hour with negative culture supernatant "Pre-GCS" indicates the BALB/c responding cells were pretreated by GCS. The stimulating cells (C57BL/6) were also divided into three groups: "B6" indicates that gamma-irradiated C57CL/6 stimulating cells were directly added to the culture of responding cells; "B6 Pre-Control" indicates that the C57BL/6 stimulating cells were pretreated for 1 hour with negative control culture supernatant, washed, gamma-irradiated, and then added to the BALB/c responder cells; "B6 Pre-GCS" indicates that the C57BL/6 stimulating cells were treated with GCS containing supernatant, washed, gamma-irradiated, and then added to the BALB/c responder cells. For each combination of cells, a 4-day MLR was performed. The results are shown in FIG. 8.

The results demonstrate that pre-treatment of stimulator cells with GCS reduced the MLR. In addition, pre-treatment of the responder cells resulted in a reduction of the MLR. Thus GCS pre-treatment affects both the stimulator and the responder cells.

EXAMPLE 9

GCS Pre-Treatment of Dendritic Cells Reduces Anti-Allo T Lymphocyte Response

Dendritic cells (DC) were generated from human monocyte cultures stimulated for 8 days with GM-CSF+IL-4. DC were propagated from adult peripheral blood, as previously described (e.g., Blauvelt A, Am J Med. 1997; 102(5B): 16–20). Briefly, PBMC were suspended in DC-media at 5–8×10$^6$ cells/ml (PBMC) in 35 mm-tissue culture plates (Costar, Cambridge, Mass.) for 2 hrs at 37° C. DC-media was is composed of RPMI 1640 medium supplemented with 10% heat-inactivated PCS (Hyclone, Logan, Utah) and 5×10$^{-5}$ M 2-ME (Gibco BRL, Gaithersburg, Md.). After this incubation, non-adherent cells were removed, and fresh DC-media was added to culture wells, supplemented with 1,000 U/ml rGM-CSF and 1,000 U/ml rhIL-4. Counterflow centrifugal elutriated monocytes were directly suspended in DC-medium at 2–4×10$^6$ cells/ml with GM-CSF and IL-4. These cells were then cultured for 7 days at 7% $CO_2$ and 37° C. Half of the volume of the media was removed on alternate days, and replaced with fresh media supplemented with the two mentioned cytokines. "G-DC" indicates dendritic cells that were incubated with GCS prior to performing the human MLR assay (see below).

To obtain T lymphocytes, PBMC were incubated with the Lympho-Kwik-T Isolation Reagent (One Lambda Inc., Canoga Park, Calif.), which depletes PBMC of all cell types except T cells by Ab-mediated, complement-dependent lysis.

A human MRL assay was then performed. In this assay, 3×10$^5$ unrelated donor T lymphocytes were stimulated with varying number of DC/GDC in a total volume of 0.2 ml complete medium. Each MLR was performed in triplicate in round microculture plates (Costar, Corning Incorporated, Corning, N.Y.) and maintained in a humidified atmosphere at 7% $CO_2$ at 37° C. The cultures were pulsed with 20 KBq/well of $^3$H-thymidine on day3, harvested 20 hours later using a Basic 96 Harvester (Skatron Instruments Inc., Sterling, Va.), and counted in a β-spectrometer (Wallac Inc., Gaithersburg, Md.).

Figure 9:
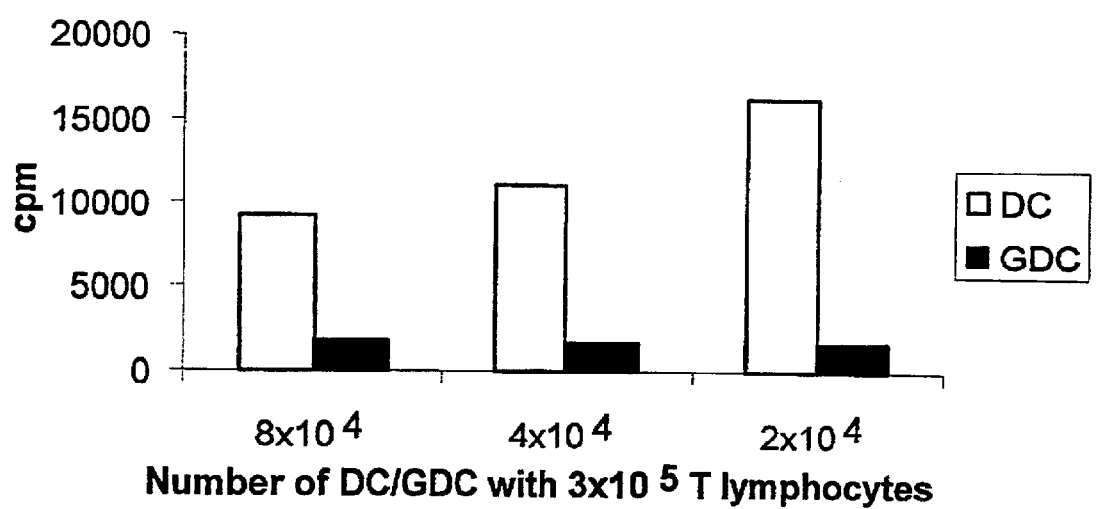
FIG. 9 is a graph showing that GCS-pretreated human monocyte-derived dendritic cells (DC) abolish a human MT. T lymphocytes from unrelated donor were used for the MLR. DC were generated from human monocyte cultures stimulated for 8 days with GM-CSF+IL-4, and one set of cultures were treated with GCS (termed GDC). The DC/GDC were irradiated with 5000 rads $\gamma$-irradiation prior to culture. Results shown are from one representative experiment.

A representative example is shown in FIG. 9. GCS pre-treatment of the dendritic cells resulted in a reduction of the anti-allogenic T cell response, as compared to the control (untreated) dendritic cells.

EXAMPLE 10

GCS Affects Monocyte Differentiation into Dendritic Cells

The nature of the effect of GCS on monocyte differentiation was subsequently demonstrated using FACS analyses. Briefly, human donor elutriated monocytes (see above) were stimulated by GM-CSF+IL-4 to differentiate to DC, in the presence or absence of GCS (1:40 final dilution) in the culture for days 1, 3 and 6. Cells were stained with monoclonal antibodies that bind to CD14 and CD1a were used in order to evaluate the differentiation of the monocytes into DC.

Briefly, at day 1, 3 6, cells were washed twice in FACS buffer (balanced salt solution, 0.1% bovine serum albumin, 0.01% sodium azide), incubated with human IgG (20 μg/ml) for 10 minutes at 4° C. to block Fc receptors, and stained with Ab that recognize the following cell surface markers: anti-CD1a-FITC and anti-CD14-PE (Pharmingen), or with isotype-matched Ab (γ1-FTTC and γ2-β-PE, Pharmingen), for 30 minutes at 4° C. The cells were then washed twice, resuspended in FACS buffer and surface expression was determined by FACS analysis, using the Becton-Dickinson FACScan software (San Jose, Calif.) and CellQuest.

Figure 10:
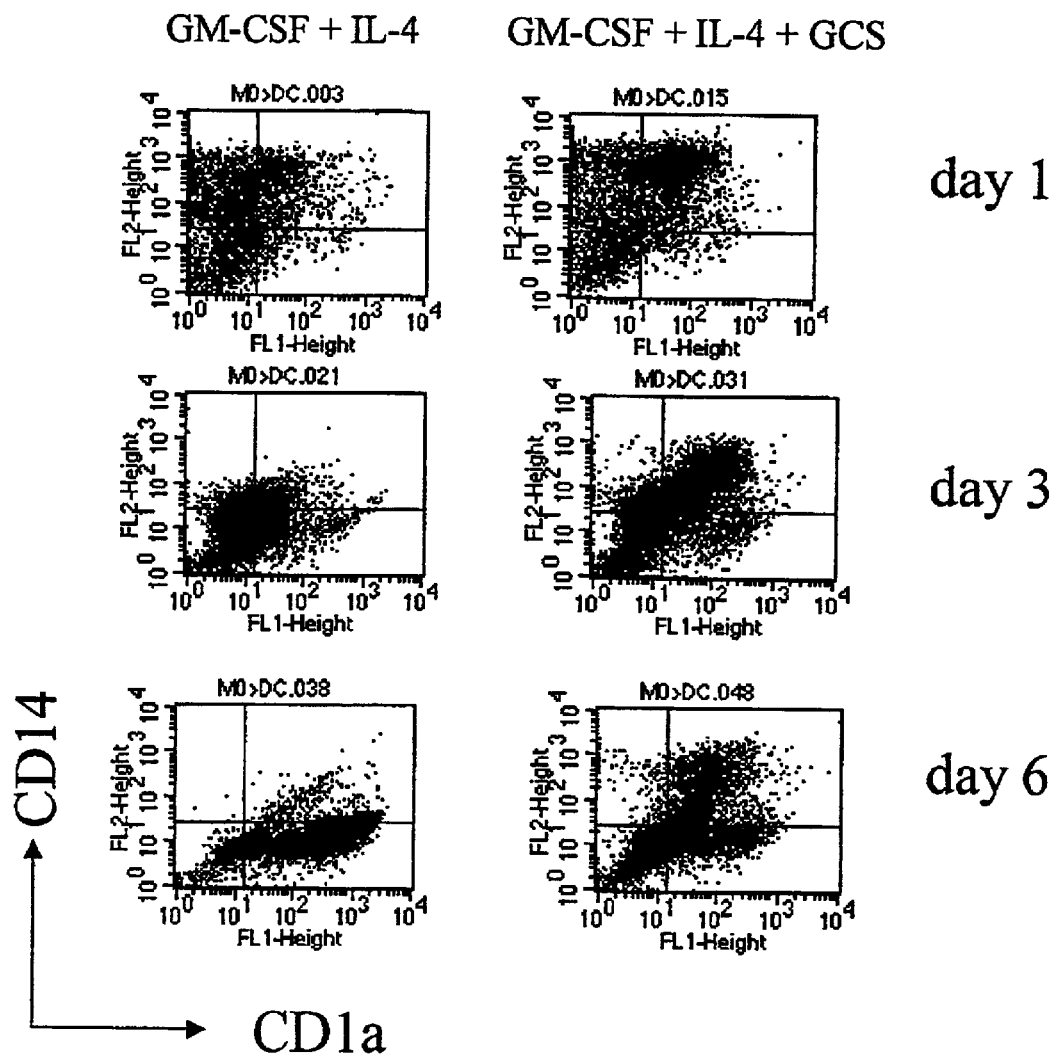
FIG. 10 shows a series of FACS plots demonstrating that GCS affects the differentiation of monocytes into dendridtic cells. Human donor monocytes were simulated with GM-CSF and IL-4 to induce differentiation to DC, with or without GCS (1:40 final dilution) in the culture (days 1, 3 and 6). Cells were stained with for anti-CD14-PE and anti-CD1a-FITC antibodies to evaluate monocyte differentiation. At 6-days of culture, monocytes cultured in the presence of GCS and GM-CFS and IL-4 exhibited an increase in bright CD14$^+$/dull CD1a$^+$ cells compared to GM-CFS and IL-4 cultures monocytes (without GCS). The absence of GCS in the differentiating cultures was also associated with a higher percentage of CD14$^-$/CD1a$^+$ (bright) matured DC.

CD1a and CD-14 expression are commonly used to evaluate the differentiation of monocytes to dendritic cells. The CD1a molecular is an important mark of maturate dendritic cells, while CD14 is a marker that is expressed on monocyte and macrophages, and is used in the identification of macrophages (see Cella, Curr. Oin.Immunol. 9: 10, 1997; Bancherau, Nature 392:245, 1998; Girolomoni, Immunol. Today 18:102, 1997). At 6-days of culture, monocytes cultured with GCS and GM-CFS+IL-4 exhibited an increase in bright CD14$^+$/dull CD1a$^+$ cells compared to GM-CFS+IL-4 cultured monocytes without GCS. Also the presence of GCS in these DC differentiating cultures was associated with a lower percentage of CD14$^-$/CD1a$^+$ (bright) matured DC (see FIG. 10). Thus, GCS affects the differentiation of monocytes into dendritic cells.

EXAMPLE 11

The Effect of GCS on Indoleamine 2,3-Dioxygennase

In order to further investigate the mechanism of action of GCS in APC, the effect on GCS on indoleamine 2,3-dioxygenase (IDO) was examined. IDO is an enzyme that is produced by macrophages that catabolizes tryptophan, an amino acid required for T lymphocyte viability and function (see Science 1998; 281:1191). For these studies, an inhibitor of IDO, 1-methyl-tryptophan M-TRP), was utilized.

Figure 11:
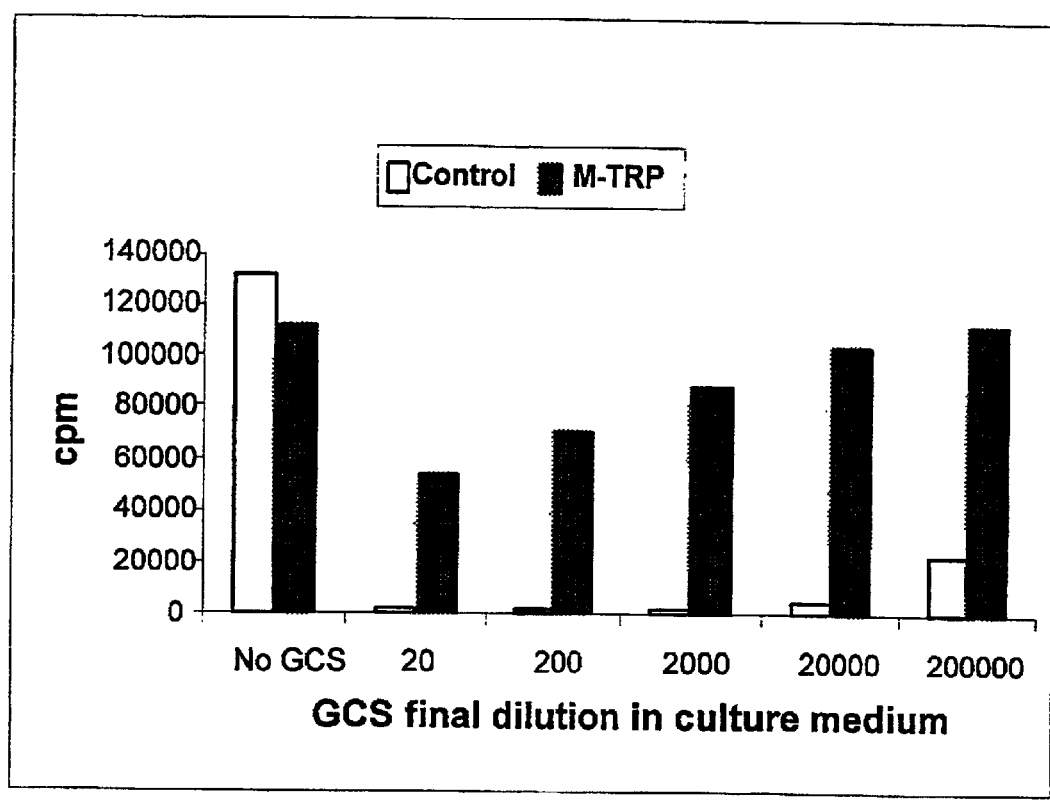
FIG. 11 is a graph showing that an indoleaminie 2,3dioxygennase (IDO) inhibitor, 1-methyl-tryptophan (1-methyl-TRP), prevents the GCS-induced supression of PHA stimulation. IDO is an enzyme produced by monocytes that catabolizes tryptophan, an amino acid required for T lymphocyte viability and function (see Science 1998; 281:1191). GCS inhibits phytohemagglutinin (PHA) induced proliferation of peripheral blood mononuclear cells (PBMC) in a dose-dependent manner (open bars). The PHA-stimulated cultures were pulsed with $^3$H- thymidine after 2 days. 1-methyl-TRP prevented the GCS-induced suppression of PHA stimulation (filled bars), demonstrating that GCS may act through this pathway.

The effect of GCS on PHA-stimulated PBMC, in the presence and absence of 1 mM 1-methyl-tryptophan was studied (M-TRP). Briefly, PHA-stimulated PBMC were prepared, as described above (see Example 8). For these studies, PHA was used as a 1:80 final dilution (GIBCO). The cells were cultured with different GCS dilutions (1:20, 1:200, 1:2000, 1:20,000, and 1:200,000) in presence or absence of M-TRP. Results of a representative experiment are shown in FIG. 11. The results demonstrate that M-TRP, an IDO inhibitor, prevented GCS-induced suppression of PHA stimulation. Thus, GCS affects the function of the enzyme IDO, and thereby can act to alter T cell viability and function.

In order to further investigate this interaction, the effect of 1-MTRP on GCS pretreated monocyte-induced, PHA stimulated T cell apoptosis was studied. In these studies, cells were stimulated with PHA and in the presence or absence of 1 mM 1-methyl-tryptophan (M-TRP). The cell population was either pre-treated with GCS, or was untreated prior to stimulation with PHA. In these studies, 5–10×10$^6$/ml monocytes were pretreated with GCS at a final dilution of 1:10 (37° C. for 1 hour), then were washed by medium for 3 times before use.

Figure 12:
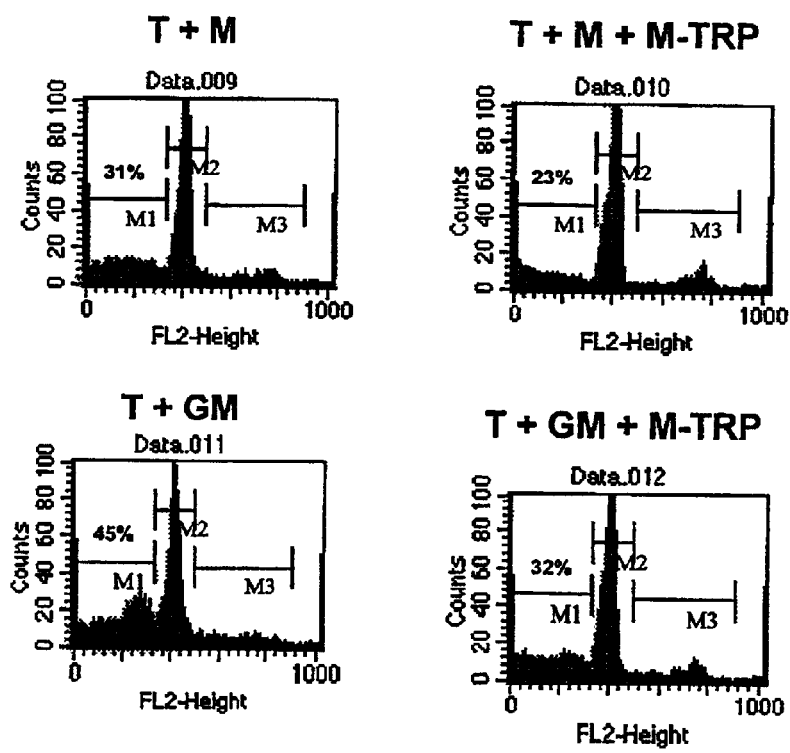
FIG. 12 shows FACS plots demonstrating that GCS pretreatment of monocytes (GM) increases PHA stimulated T lymphocyte apoptosis (T+GM=45%) compared to monocytes (M) not treated with GCS (T+M=31%), 1-methyl-tryptophan (M-TRP) reduced T lymphocyte apoptosis in control cultures (T+M+M-TRP=23%) and in GCS-treated monocyte+T cells (T+GM+M-TRP=32%). (Note T=T lymphocytes; M=monocytes; GM=GCS-pretreated monocytes).

Following stimulation, the cells were stained with propidium iodide (PI), and the fluorescence of individual cells was analyzed by flow cytometry using a FACScan (Becton Dickinson, San Jose, Calif.). The results are shown in the flow diagrams presented in FIG. 12. In this figure, GCS pretreated monocytes are indicated as "GM," while untreated monocytes are indicated as "M." Inclusion of M-TRP in the culture is indicated as "M-TRP." All cultures include T cells ("T"). The areas of the fluorescent profiles used for the analyses are indicated as "M1," "M2," and "M3."

GCS pretreatment of monocytes (GM) increased T lymphocyte apoptosis (T+GM=45%) compared to untreated monocytes (T+M=31%). In addition, 1-methyl-tryptophan (M-TRP) reduced T lymphocyte apoptosis in control cultures (T+M+M-TRP=23%) and in GCS-treated monocyte+T cells (T+GM+M-TRP=32%). 1-methyl-tryptophan also affected GCS induced T cell apoptosis (compare T+GM (45%) with T+GM+M-TRP(32%)).

Figure 13:
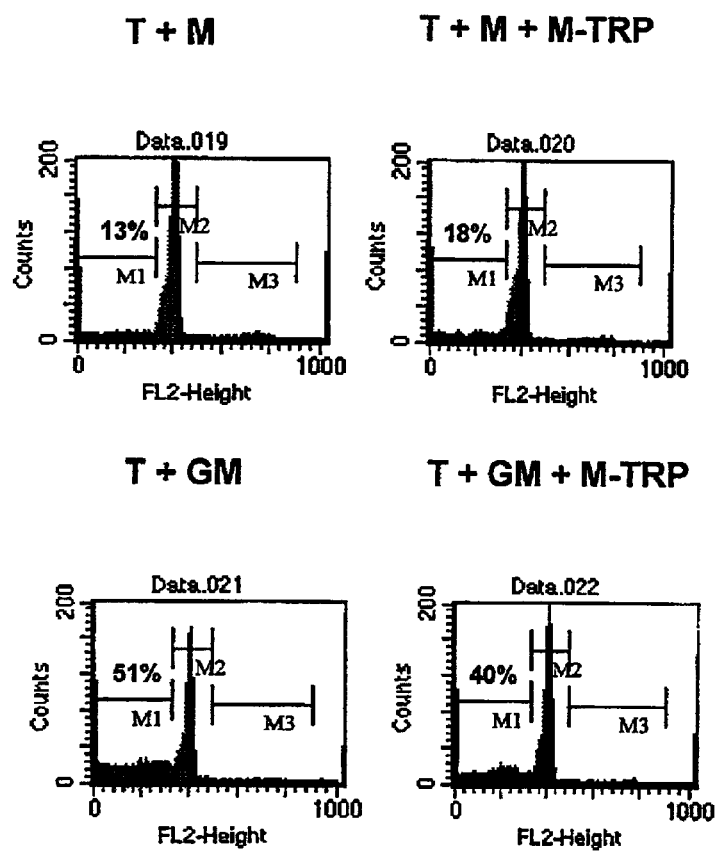
FIG. 13 shows FACS plots demonstrating that GCS pretreatment of monocytes (GM) increases recall antigen mixture (consisting of influenza A virus, tetanus toxoid and candida) stimulated T lymphocyte apoptosis (T+GM=51%) compared to monocytes (M) not treated with GCS (T+M= 13%). The inhibitor 1-methyl-tryptophan (M-TRP) reduced T lymphocyte apoptosis in control cultures (T+M+M-TRP= 18%) and in GCS-treated monocyte+T cells (T+GM+M-TRP=40%).

The effect of M-TRP on GCS-pretreated monocyte-induced, reacall antigen T cell apoptosis was also investigated (see FIG. 13). The recall antigen was a mixture of influenza A virus (FLU), tetanas toxoid CTT) and candida (CASTA) (as described above in Example 1). In this assay system, GCS pretreatment of monocytes (GM) increases T lymphocyte apoptosis (T+GM=51%) compared to untreated monocytes+M=13%). The inclusion of 1-methyl-tryptophan (M-TRP) increased T lymphocyte apoptosis in control cultures (T+M+M-TRP=18%) as compared to control cultures (T+M=13%). The inclusion of 1-methyl-tryptophan (M-TRP) in GCS-treated monocyte+T cells (T+GM+M-TRP=40%, decreased T lymphocyte apoptosis as compared to GCS pretreatment of monocytes in the absence of M-TRP (T+GM=51%).

EXAMPLE 12

GCS Treatment To Reduce Autoimmune Response to MS Autoantigenic Protein, MBP

For the pilot autoimmune study, SJL mice (Sakai et al., J. Neuroimmunol. 19:21–32, 1988) a strain genetically susceptible to the induction of multiple sclerosis (MS), are inoculated iv with approximately $5 \times 10^7$ syngeneic APC that have been treated with GCS (see Example 5) and pulsed with myelin basic protein (MBP) peptide (e.g. see Vergelli et al, Eur. J. Immunol. 26:2624–34, 1996; Gautam et al., J. Exp. Med. 176:605–9, 1992). In one embodiment, the APC are treated with GCS simultaneously with the exposure to the MBP peptide. In another embodiment, the APC are exposed to GCS at a different time than the exposure to the MBP peptide.

Two to four weeks later, the treated and untreated mice are immunized with MBP (see Zamvil et al., Nature 324:258–60, 1986) under conditions that induce MS, and the development or progression of MS is evaluated (see Encinas et al., J. Immunol. 157:2186–92, 1996). Treatment with the APC decreases the symptoms or slows the progression of MS in this model system.

In another sandy, mice are immunized with MBP, and subsequently given the GCS-treated, peptide-pulsed APCs (see example 5). The development and/or progression of MS is then evaluated. GCS-treated, peptide-pulsed APCs decreases the symptoms or slows the progression of MS in this animal model system.

REFERENCES

Agrawal, B. et al. 1998. *Nat. Med.* 4(1): 43–49.
Banchereau, J., and R. M. Steinman. 1998. *Nature* 392: 245–252.
Behrens B. C. et al. 1987. *Cancer Res* 47:414–418
Bodmer, S. et al. 1989. *J. Immunol.* 143: 3222–3229.
Brooks, W. H. et al. 1972. *J. Exp. Med.* 136: 1631–1647.
Brooks, W. H. et al. 1981. *J. Neurosurg.* 54: 331–337.
Chougenet, C. et al. 1998. *Eur. J. Immunol.* 28:646–656.
Clerici, M. et al. 1994. *J. Clin. Invest.* 93: 768–775.
Clerici, M. et al. 1998. *J. Nat. Cancer Inst.* 90: 261–263.
de Waal Malefyt, R. et al. 1991. *J. Exp. Med.* 174: 915–924.34.
de Ridder. L. I. et al. 1987. *Acta Neuropathol (Berl)* 72: 207–213
Elliott, L. H. et al. 1984. *J. Immunol.* 132: 1208–1215.
Elliott. L. H. et al. 1990a. *J. Nat. Cancer Inst.* 75: 919–922.
Elliott, L. H. et al. 1990b. *J. Clin. Invest.* 86: 80–86.
Elliott, L. H. et al. 1992. *J. Neuro-Oncology* 14: 1–7.
Fox, F. E. et al. 1997. *J. Invest. Dermatol.* 108: 43–48.
Fujiwara, H., and T. Hamaka. 1995. *Immunol. Res.* 14: 271–291.
Gruss, H-J. et al. 1997. *Immunol. Today* 18: 156–163.
Kalinski, P. et al. 1997. *J. Immunol.* 159:28–35.
Mahaley, M. S. et al. 1977. *J. Neurosurgery* 46:463–476.
Morford, L. A. et al. 1997. *J. Immunol.* 159: 4415–4425.
Roszman, T. L. et al. 1987. *J. Neurosurg.* 67: 874–879.
Schmacher, R., ed. 1993. Primer on the Rheumatic Diseases, pp. 100–105.
van der Pouw Kraan, T. C. T. M. et al. 1995. *J. Exp. Med.* 181:775–779.
Wrann, M. et al. 1987. *EMBO J.* 6: 1633–1636.

We claim:

1. A method of selectively inhibiting an immune response to one or more selected autoantigenic protein antigens of multiple sclerosis comprising:

exposing purified or isolated antigen presenting cells (APCs), which present an autoantigenic protein antigen of multiple sclerosis against which selective inhibition of an immune response is desired, to an immunosuppressive composition comprising one or more factors secreted by a glioblastoma cell, wherein the one or more factors secreted by the glioblastoma cells have the following characteristics:
  (a) induce APCs to induce T cells to undergo apoptosis;
  (b) molecular weight greater than about 40 kDa;
  (c) ability to bind to anion, but not cation, exchange columns;
  (d) maintain an ability to induce APCs to induce T cells to undergo apoptosis (i) within the pH range of 2 to 11, (ii) following heat exposure up to 56° C., and (iii) following immunoprecipitation of TGF-β1, TGF-β2, TGF-β3, IL-6, calcitonin gene related peptide (CGRP), and M-CSF from the composition; and
  (e) lose the ability to induce APCs to induce T cells to undergo apoptosis (i) following heat exposure above 56° C., or (ii) after exposure to trypsin; and introducing a therapeutically effective amount of the APCs exposed to the immunosuppressive composition into a subject in whom a selectively inhibited immune response to the antigen is desired, wherein introduction of the APCs inhibits the immune response of the subject to the antigen.

2. A method of selectively inhibiting an immune response to one or more selected autoantigenic protein antigens of multiple sclerosis, comprising:

exposing purified or isolated antigen presenting cells (APCs), comprising macrophages, monocytes, dendritic cells, and/or B cells, to an immunosuppressive composition comprising one or more factors secreted by one or more glioblastoma cells,
  wherein the APCs present an autoantigenic protein antigen of multiple sclerosis against which selective inhibition of an immune response is desired;
  and wherein incubation of the APCs with the one or more factors results in effects comprising:
    (a) decreasing expression of MHC class II antigens and CD 80/86 on the surface of the monocytes and the dendritic cells,
    (b) increasing expression of IL-10 in the monocytes and dendritic cells, and
    (c) decreasing the expression of IL-12 in the monocytes and dendritic cells;
  and wherein the one or more factors secreted by the glioblastoma cells have the following characteristics:

(1) induce APCs to induce T cells to undergo apoptosis;
(2) molecular weight greater than about 40 kDa;
(3) ability to bind to anion, but not cation, exchange columns;
(4) maintain an ability to induce APCs to induce T cells to undergo apoptosis (i) within the pH range of 2 to 11, (ii) following heat exposure up to 56° C., and (iii) following immunoprecipitation of TGF-β1, TGF-β2, TGF-β3, IL-6, calcitonin gene related peptide (CGRP), and M-CSF from the composition; and
(5) lose the ability to induce APCs to induce T cells to undergo apoptosis (i) following heat exposure above 56° C., or (ii) after exposure to trypsin; and introducing a therapeutically effective amount of the APCs exposed to the immunosuppressive composition into a subject in whom a selectively inhibited immune response to the antigen is desired, wherein introduction of the APCs inhibits the immune response of the subject to the antigen.

3. The method of claim 1, wherein the APCs are repetitively exposed to one or more peptide fragments of the autoantigenic protein simultaneously with exposing said APC to said immunosuppressive composition.

4. The method of claim 1, wherein the autoantigenic protein is myelin basic protein (MBP).

5. The method of claim 1, wherein the APCs are selected from the group consisting of monocytes, macrophages, and dendritic cells.

6. The method of claim 5, wherein the APCs consist of monocytes.

7. The method of claim 3, wherein the APCs comprise monocytes isolated or purified from the subject's blood.

8. The method of claim 2, wherein the glioblastoma cell is selected from the group consisting of SNB 19 (DSMZ no. 325), A172 (ATCC no. CRL-1620), U87 MG (ATCC no. HTB-14), U138 MG (ATCC no. HTB-16) and U373 MG (ECACC no.89081403).

9. The method of claim 2, wherein introducing the APCs into the subject comprises administering the APCs by a route selected from the group consisting of intravenous, subcutaneous, intramuscular, and intraperitoneal administration.

10. A method of selectively inhibiting an immune response to one or more selected autoantigenic protein antigens of multiple sclerosis comprising:

exposing purified or isolated antigen presenting cells (APCs), which present an autoantigenic protein antigen of multiple sclerosis against which selective inhibition of an immune response is desired, to an immunosuppressive composition comprising one or more factors secreted by a glioblastoma cell, wherein the one or more factors secreted by the glioblastoma cell have the following characteristics:

(a) induce APCs to induce T cells to undergo apoptosis;
(b) molecular weight greater than about 40 kDa;
(c) ability to bind to anion, but not cation, exchange columns;
(d) maintain an ability to induce APCs to induce T cells to undergo apoptosis (i) within the pH range of2 to 11, (ii) following heat exposure up to 56° C., and (iii) following immunoprecipitation of TGF-β1, TGF-β2, TGF-β3, IL-6, calcitonin gene related peptide (CGRP), and M-CSF from the composition; and
(e) lose the ability to induce APCs to induce T cells to undergo apoptosis (i) followings heat exposure above 56° C., or (ii) after exposure to trypsin; and introducing a therapeutically effective amount of the APCs exposed to the immunosuppressive composition into a subject in whom a selectively inhibited immune response to the antigen is desired, wherein introduction of the APCs inhibits the immune response of the subject to the antigen;

wherein the glioblastoma cell is selected from the group consisting of SNB 19 (DSMZ no. 325), A172 (ATCC no. CRL-1620), U87 MG (ATCC no. HTB-14), U138 MG (ATCC no. HTB-16), U373 MG (ECACC no. 89081403), T98G (ATCC no. CRL-1690), DBTRG-05MG (ATCC no. CRL-2020), M059K (ATCC no. CRL-2365), M059J (ATCC no. CRL-2366), and U118 MG (ATCC no. HTB-15).

11. The method of claim 10, wherein incubation of monocytes, dendritic cells, and B cells with the one or more factors results in effects comprising:

(a) decreased expression of MHC class II antigens and CD 80/86 on the surface of the monocytes and the dendritic cells, without substantial effect on the expression of MHC class II antigens and CD 80/86 on the B cells;
(b) increased expression of IL-10 in monocytes and dendritic cells; and
(c) decreased the expression of IL-12 in monocytes and dendritic cells.

12. The method of claim 2, wherein the glioblastoma cell is selected from the group consisting of T98G (ATCC no. CRL-1690), DBTRG-05MG (ATCC no. CRL-2020), M059K (ATCC no. CRL-2365), M059J (ATCC no. CRL-2366), and U118 MG (ATCC no. HTB-15).

13. The method of claim 2, wherein the autoantigenic protein is myelin basic protein (MBP).

14. The method of claim 10, wherein the autoantigenic protein is myelin basic protein (MBP).

* * * * *